US009447304B2

(12) United States Patent
Drumheller et al.

(10) Patent No.: US 9,447,304 B2
(45) Date of Patent: Sep. 20, 2016

(54) COATING FOR A SURFACE

(71) Applicant: W. L. Gore & Associates, Inc., Newark (DE)

(72) Inventors: Paul D. Drumheller, Flagstaff, AZ (US); Charles D. Claude, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 0 days.

(21) Appl. No.: 14/209,866

(22) Filed: Mar. 13, 2014

(65) Prior Publication Data

US 2014/0271774 A1 Sep. 18, 2014

Related U.S. Application Data

(60) Provisional application No. 61/785,999, filed on Mar. 14, 2013.

(51) Int. Cl.
| | | |
|---|---|---|
| *A61L 31/10* | (2006.01) | |
| *A61L 27/34* | (2006.01) | |
| *A61L 29/08* | (2006.01) | |
| *C09D 5/00* | (2006.01) | |
| *C09D 179/02* | (2006.01) | |
| *B05D 3/06* | (2006.01) | |
| *C09D 131/04* | (2006.01) | |

(52) U.S. Cl.
CPC ............ *C09D 179/02* (2013.01); *A61L 27/34* (2013.01); *A61L 29/085* (2013.01); *A61L 31/10* (2013.01); *B05D 3/065* (2013.01); *C09D 5/002* (2013.01); *C09D 131/04* (2013.01); *A61L 2420/06* (2013.01); *Y10T 428/31544* (2015.04); *Y10T 428/31725* (2015.04)

(58) Field of Classification Search
CPC ...... B05D 1/185; B05D 5/00; B05D 7/5483; C02F 1/281; C02F 1/285; C02F 1/288; C02F 2101/20; C08J 7/123; C09D 179/04; C09D 5/1662; C09D 5/4407; C23C 18/1608; C23C 18/1803; C23C 18/1834; C23C 18/1844; C23C 18/2006; C23C 18/2066; C23C 18/31; C23C 18/40; C23C 18/42
See application file for complete search history.

(56) References Cited

U.S. PATENT DOCUMENTS

| | | |
|---|---|---|
| 5,705,703 A | 1/1998 | Bernauer et al. |
| 7,087,658 B2 | 8/2006 | Swan et al. |
| 7,094,418 B2 | 8/2006 | Chudzik et al. |
| 7,550,443 B2 | 6/2009 | Stucke et al. |
| 7,659,219 B2 | 2/2010 | Biran et al. |
| 2002/0120333 A1* | 8/2002 | Keogh ................... A61L 27/34 623/11.11 |
| 2004/0044404 A1* | 3/2004 | Stucke .................. A61L 29/085 623/1.46 |
| 2004/0063805 A1* | 4/2004 | Pacetti .................... A61L 31/10 523/113 |
| 2008/0149566 A1 | 6/2008 | Messersmith et al. |
| 2010/0330025 A1 | 12/2010 | Messersmith et al. |
| 2011/0039960 A1 | 2/2011 | Xu et al. |
| 2011/0065085 A1 | 3/2011 | Biran et al. |
| 2011/0136704 A1 | 6/2011 | Sharma et al. |
| 2011/0250353 A1 | 10/2011 | Caruso et al. |

FOREIGN PATENT DOCUMENTS

| | | |
|---|---|---|
| WO | WO2004/020012 | 3/2004 |
| WO | WO2008/049108 | 4/2008 |
| WO | WO2010/006196 | 1/2010 |
| WO | WO2010/101863 | 9/2010 |
| WO | WO2011/005258 | 1/2011 |
| WO | WO2012/032283 | 3/2012 |

OTHER PUBLICATIONS

Wei et al., Polym. Chem., 2010, 1, 1430-1433.*
Del Frari et al., Degradation of Polydopamine Coatings by Sodium Hypochlorite: A Process Depending on the Substrate and the Film Synthesis Method, Polymer Degradation and Stability 2012, 97(9), pp. 1844-1849.
Dreyer et al., Elucidating the Structure of Poly(dopamine), Langmuir 2012, 28 pp. 6428-6435.
Drumheller et al., Polymer Networks with Grafted Cell Adhesion Peptides for Highly Biospecific Cell Adhesive Substrates, Analytical Biochemistry, 1994, 222, pp. 380-388.
Herlinger, E., Spontaneous Autooxidation of Dopamine, Journal of the Chemical Society, Perkin Transactions 2 1995, pp. 259-263.
Hong, et al., Non-Covalent Self-assembly and Covalent Polymerization Co-Contribute to Polydopamine Formation, Advanced Functional Materials 2012, 22, pp. 4711-4717.
Jiang et al, Surface modification of PE Porous Membranes based on the Strong Adhesion of Polydopamine and Covalent Immobilization of Heparin, Journal of Membrane Science 2010, 364(1-2, pp. 194-202.
Ju et al., Bioinspired Polymerization of Dopamine to Generate Melanin-Like Nanoparticles Having an Excellent Free-Radical-scavenging Property, Biomacromolecules 2011, 12, pp. 625-632.

(Continued)

*Primary Examiner* — Abigail Fisher

(74) *Attorney, Agent, or Firm* — Carol A. Lewis White

(57) ABSTRACT

Coatings for a surface, especially a priming coating, of the present invention have been found to be durable, resistant to oxidative degradation, erosion and depolymerization, stable to sterilization and low particulating, and are easily applied to the required surface of a substrate in a surface-independent manner. Such coatings, when used as priming coatings to be coated with a subsequent coating, in at least some embodiments, form exterior coatings which are also highly durable and are stable to sterilization and aging.

3 Claims, 4 Drawing Sheets

(56) References Cited

OTHER PUBLICATIONS

Kang et al., A Biofunctionalization Scheme for Neutral Interfaces Using Polydopamine Polymer, Biomaterials 2011, 32(27), pp. 6374-6380.
Kang et al., Bioinspired Single Bacterial Cell Force Spectroscopy, Langmuir Letter, 2009, 25(17), pp. 9656-9659.
Kang et al., One-Step Multipurpose Surface Functionalization by Adhesive Catacholamine, Advanced Functional Materials 2012, 22(14), pp. 2949-2955.
Kim et al., Mussel-Inspired Block Copolymer Lithography for Low Surface Energy Materials of Teflonk, Graphene, and Gold, advanced Materials 2011, 23(47), pp. 5518-5622.
Lee et al., Facile Conjugation of Biomolecules onto Surfaces Via Mussel Adhesive Protein Inspired Coatings, Advanced Materials 2009, 21(4), pp. 431-434.
Lee et al., Mussel-Inspired Adhesives and Coatings, Annual Review of Materials research 2011, 41, pp. 99-132.
Lee, Haeshin, Rho Junsung, Messersmith, Phillip B., Mussel-Inspired Surface Chemistry for Multifunctional Coatings, Science 2007, 318, pp. 426-430.
Lee et al., Synthesis and Gelation of DOPA-Modified Poly(ethylene glycol) Hydrogels, Biomacromolecules 2002, 3(5), pp. 1038-1047.
Liu et al., Amination of Surfaces Via Self-assembly of Dopamine, Journal of Colloid and Interface Science 2011, 362(1), pp. 127-134.
Sun et al., Facile and Universal Immobilization of L-lysine Inspired by Mussels, Journal of Materials Chemistry 2012, 22, pp. 10035-10041.
Swanson et al., Photochemical Surface Modification of Polymers for Improved Adhesion, Journal of Adhesion Science and Technology 1995, 9(3), pp. 385-391.
Tsai et al., Dopamine-Assisted Immobilization of Poly(ethylene imine) Based Polymers for Control of Cell-surface Interations, Acta Biomaterialia 2011, 7(6), pp. 2518-2525.
Zhang et al., A Facile Approach to Surface Modification on Versatile Substrates for Biological Applications, Journal of Materials Cemistry 2012, 22, pp. 17159-17166.
Zhao et al., Oxidant-Induced Dopamine Polymerization for Multifunctional Coatings, Polymer Chemistry 2010, 1, pp. 1430-1433.
International Search Report, PCT/US2014/027273, Aug. 7, 2014, 5 pages.

\* cited by examiner

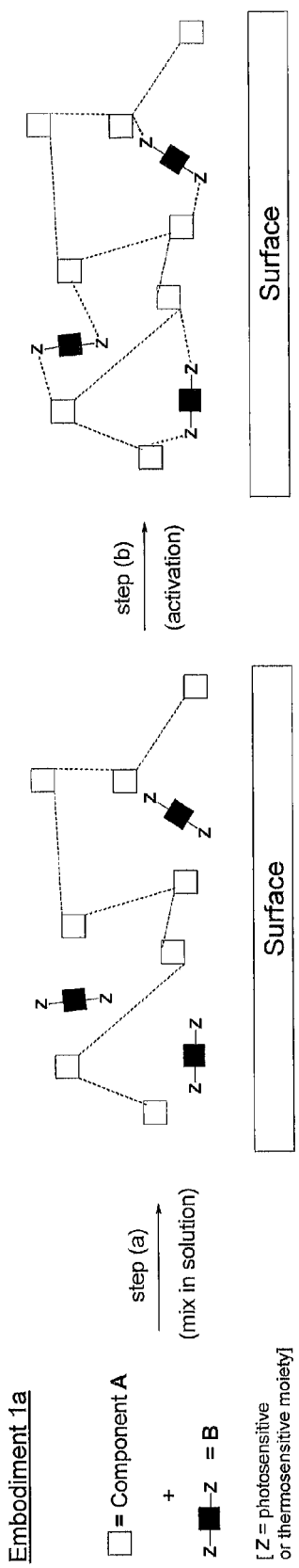
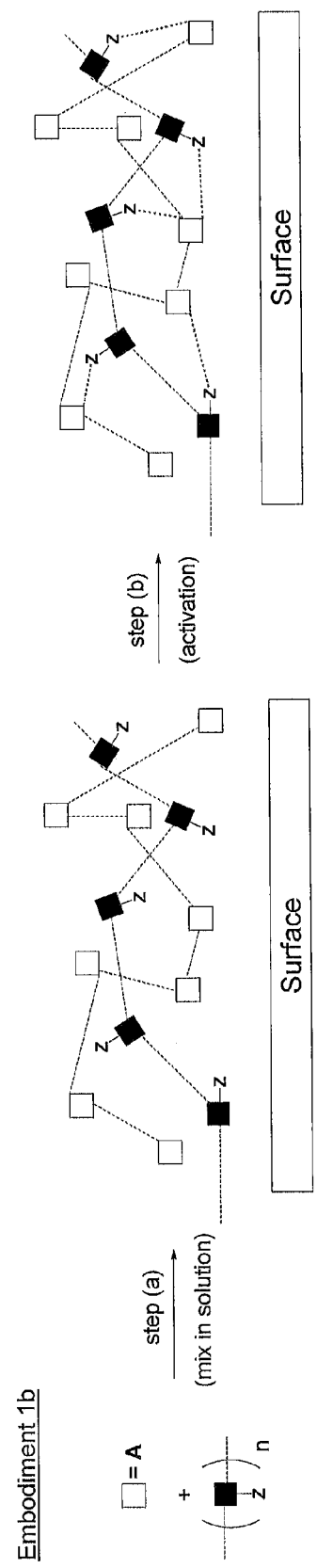

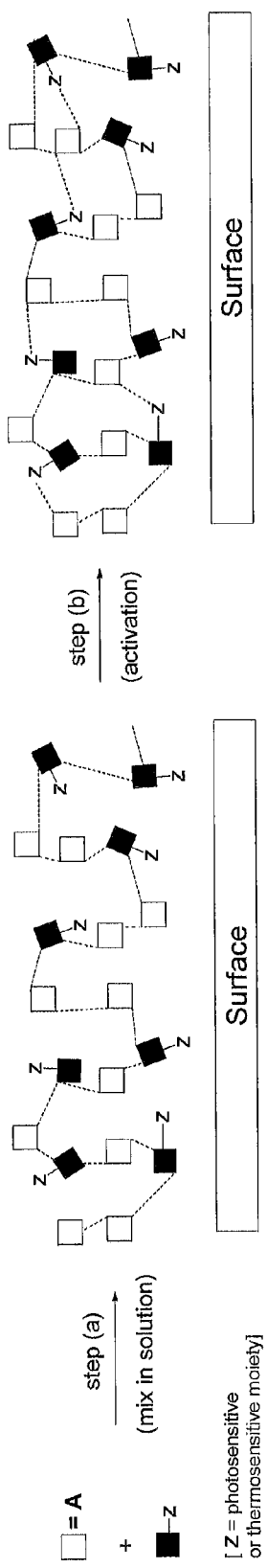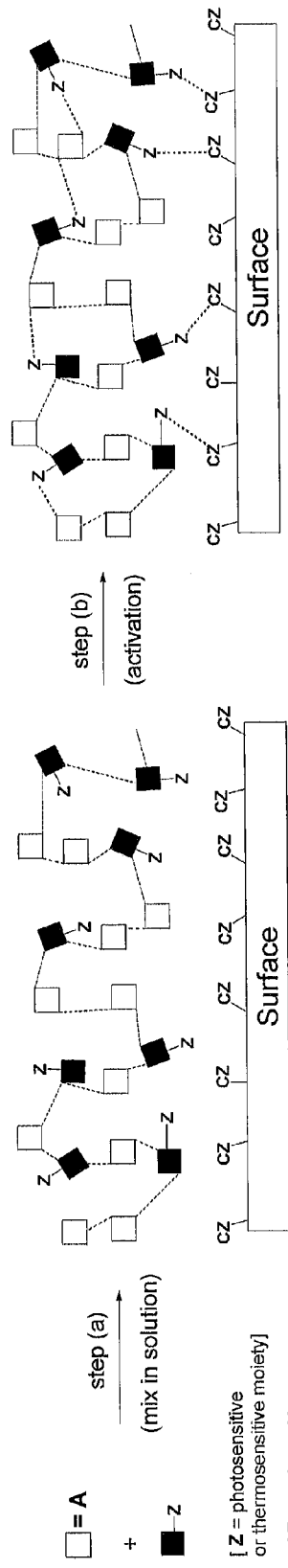

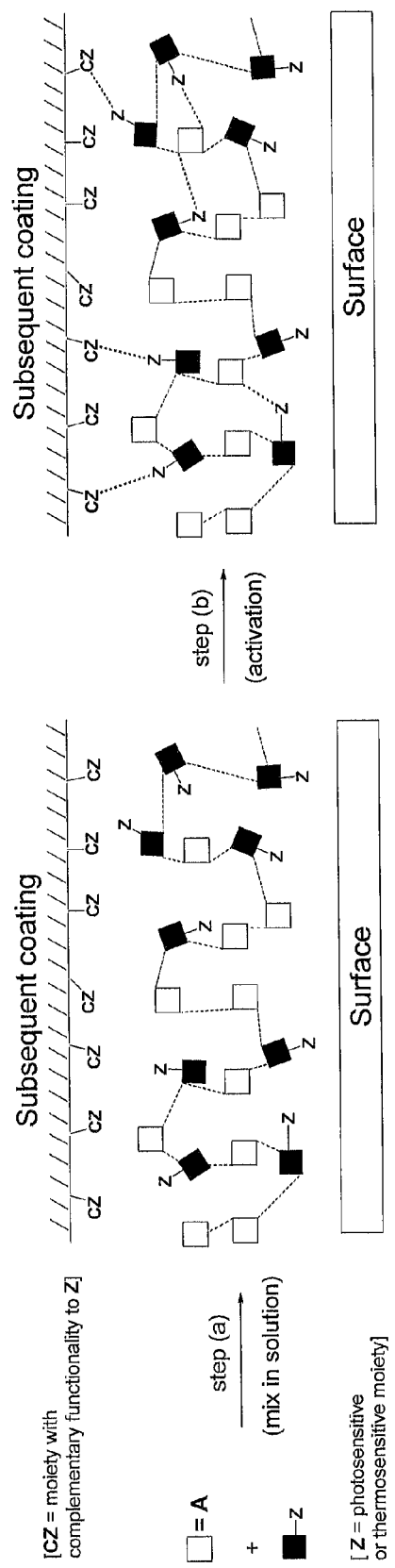

COATING FOR A SURFACE

FIELD OF THE INVENTION

The present invention relates to a coating for a surface, especially a priming coating, and to methods for preparing such a coating.

BACKGROUND OF THE INVENTION

A priming coating is a preparatory coating that is applied to a surface before a subsequent coating is applied. Priming coatings are used in a broad range of applications, inter alia, to improve the adhesion between the subsequent coating and the surface, to increase the durability of the subsequent coating, and to provide additional protection for the surface being coated.

The use of polydopamine as a primer has attracted great interest since the discovery that simple immersion of a substrate in a dilute aqueous solution of dopamine, buffered to alkaline pH, results in the spontaneous deposition of a polydopamine film on the substrate. Messersmith et al., (Science, 2007, 318, 426-430) demonstrated that a polydopamine coating is able to form on a variety of substrate surfaces, including metals, metal oxides, ceramics, synthetic polymers and a wide range of other hydrophilic and hydrophobic materials. Polydopamine coatings have been used as a platform for the conjugation of synthetic polymers or biomolecules to a surface, as illustrated in WO2011/005258 which discloses the attachment of amine-functionalised polyethylene glycol ("PEG-NH$_2$") to a polydopamine coating, to provide a hydrophilic outer layer for the prevention of biofilm formation. US2008/0149566 discloses that a substrate treated with a surface-modifying agent (SMA) such as polydopamine can be treated with a secondary reactive moiety to impart specific functionalities to the substrate. The secondary moiety is described as an "ad-layer" and may be applied by various means, including by nucleophilic addition and by free radical graft polymerisation.

However, the use of polydopamine as a coating such as a priming coating has certain drawbacks. Polydopamine is known to degrade under oxidative conditions and is also susceptible to degradation under sterilising conditions, thereby reducing its utility for coating medical devices. Although the exact nature of the interaction between a polydopamine coating and the surface which it coats is unknown and is likely to be surface dependent, it is acknowledged the polydopamine layer is not covalently bound to the surface. This has implications for the durability of any subsequent coating that is applied to the polydopamine layer. Furthermore, it has been observed that when a substrate is dipped in a solution of polydopamine, over time particulates of polydopamine are observed in the solution. Particulation is undesirable in most coating applications that require a long-term or permanent, stable coating.

In summary, there remains a need for improved coatings for surfaces, particularly priming coatings. Preferably, such coatings are durable, sterilizable, low particulating, biocompatible and readily applied to a surface.

SUMMARY OF THE INVENTION

In one aspect, the invention provides a surface having a coating comprising a mixture of components A and B, wherein component A is a polymer formed by self-polymerisation of a molecule comprising catechol functionality and amine and/or amide and/or hydroxyl functionality; and component B is
(i) a cross-linking molecule comprising two or more photosensitive or thermosensitive moieties, at least some of which moieties form covalent bonds with component A; or
(ii) a polymer comprising photosensitive or thermosensitive moieties at least some of which moieties form covalent bonds with component A and which polymer forms an interpenetrating network with component A;
or a mixture thereof.

In another aspect, the invention provides a surface having a coating comprising a cross-linked copolymer of components A and B, wherein component A is a molecule capable of self-polymerisation comprising catechol functionality and amine and/or amide and/or hydroxyl functionality; and component B is a molecule comprising one or more groups capable of participating in the polymerisation of component A, wherein said molecule comprises one or more photosensitive or thermosensitive moieties capable of forming covalent bonds with component A, at least some of which moieties form covalent bonds with component A in the copolymer.

In a further aspect, the invention provides a method of coating a surface, comprising the steps of:
(a) contacting the surface with a mixture comprising components A and B, wherein
component A is a molecule capable of self-polymerisation comprising catechol functionality and amine and/or amide and/or hydroxyl functionality; and component B is
(i) a cross-linking molecule comprising two or more photosensitive or thermosensitive moieties capable of forming covalent bonds with component A; or
(ii) a polymer comprising photosensitive or thermosensitive moieties capable of forming covalent bonds with component A;
or a mixture thereof;
such that component A self-polymerises in the presence of component B and in the case of (ii) forms an interpenetrating network with component B; and
(b) activating the photosensitive or thermosensitive moieties of component B such that at least some of said moieties form covalent bonds with component A.

In a still further aspect, the invention provides a method of coating a surface, comprising the steps of:
(a) contacting the surface with a mixture comprising components A and B, wherein
component A is a molecule capable of self-polymerisation comprising catechol functionality and amine and/or amide and/or hydroxyl functionality; and
component B is a molecule comprising one or more groups capable of participating in the polymerisation of component A, wherein said molecule comprises one or more photosensitive or thermosensitive moieties capable of forming covalent bonds with component A such that a copolymer of components A and B is formed; and
(b) activating the photosensitive or thermosensitive moieties of component B in the copolymer such that at least some of said moieties form covalent bonds with component A.

As explained in the Examples, coatings of the present invention, in at least some embodiments, have been found to be durable, resistant to oxidative degradation, erosion and depolymerisation, stable to sterilization and low particulating, and are easily applied to the required surface of a substrate in a surface-independent manner. Such coatings, when used as priming coatings to be coated with a subsequent coating, in at least some embodiments, form exterior coatings which are also highly durable and are stable to sterilisation and aging.

BRIEF DESCRIPTION OF THE FIGURES

FIG. 2: shows Embodiment 1a of the invention, wherein component B is a cross-linking molecule comprising two or more photosensitive or thermosensitive moieties capable of forming covalent bonds with component A;

FIG. 3: shows Embodiment 1b of the invention, wherein component B is a polymer comprising photosensitive or thermosensitive moieties capable of forming covalent bonds with component A;

FIG. 4: shows Embodiment 2 of the invention, wherein component B is a molecule comprising one or more groups capable of participating in the polymerisation of component A, wherein said molecule comprises a photosensitive or thermosensitive moiety capable of forming covalent bonds with component A such that a copolymer of components A and B is formed;

FIG. 5: shows Embodiment 2 of the invention, wherein the resulting coating is covalently bonded to the surface;

FIG. 6: shows Embodiment 2 of the invention, wherein a subsequent coating is covalently bonded to the priming coating of the invention.

DETAILED DESCRIPTION OF THE INVENTION

Figure 1:
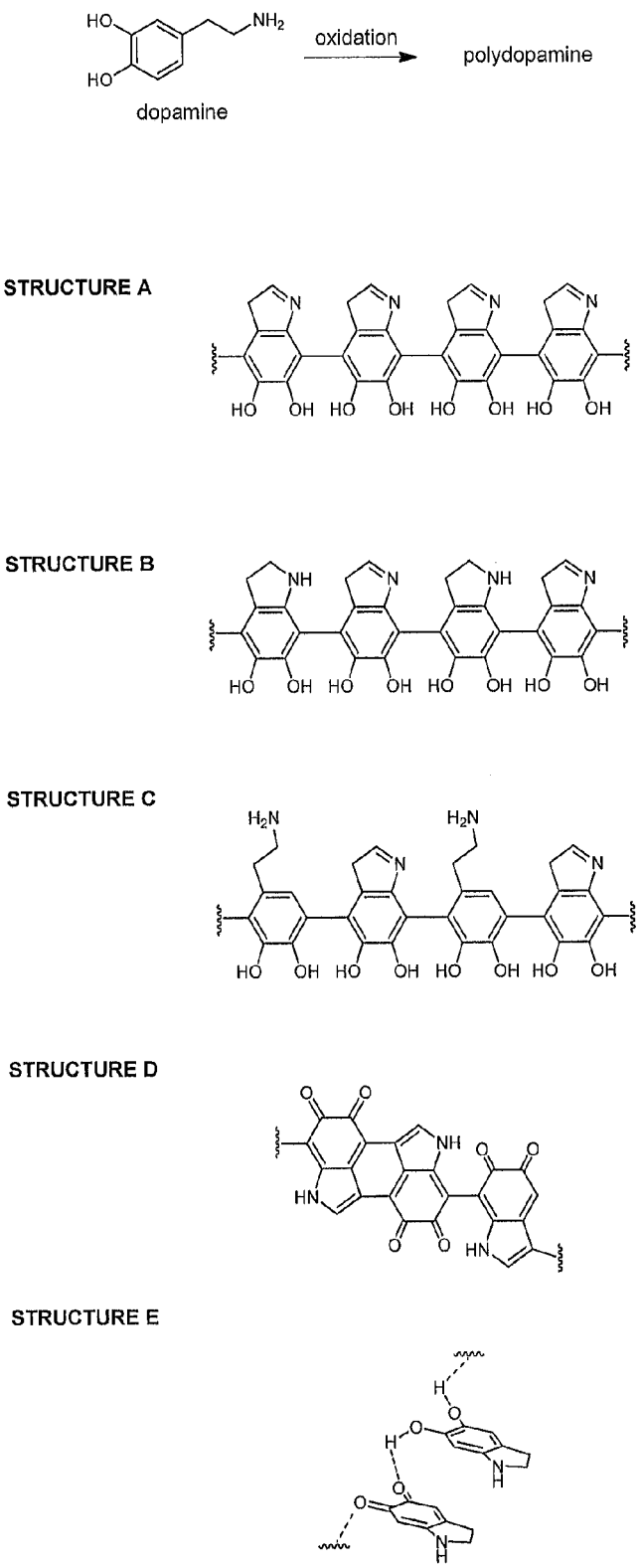
FIG. 1: shows various proposed structures for polydopamine.

The present invention relates to a coating, especially a priming coating, which is applied to a surface. In one embodiment the surface is the surface of a substrate.

Substrate

Suitable substrates may include, but are not limited to, industrial and consumer articles such as membranes and fabrics, medical devices, analytical devices, separation devices. The present invention also has applications in diagnostic devices such as nanoarrays and microarrays.

Medical Devices

For the purposes of this invention, the term "medical device" refers to intracorporeal or extra-corporeal devices but more usually to intracorporeal medical devices.

Thus, in one embodiment, the surface is the surface of a substrate comprising a medical device. In another embodiment, the surface is the surface of a substrate comprising an intracorporeal medical device. In a further embodiment, the surface is the surface of substrate comprising an extracorporeal medical device. In another embodiment, the surface is the surface of a substrate which is a component of a medical device.

Examples of intracorporeal medical devices which can be permanent or temporary intracorporeal medical devices include stents including bifurcated stents, balloon expandable stents, self-expanding stents, stent-grafts including bifurcated stent-grafts, grafts including vascular grafts, bifurcated grafts, dialators, vascular occluders, embolic filters, embolectomy devices, artificial blood vessels, blood indwelling monitoring devices, artificial heart valves (leaflet, frame, and/or cuff), pacemaker electrodes, guidewires, cardiac leads, cardiopulmonary bypass circuits, cannulae, plugs, drug delivery devices, balloons, tissue patch devices, blood pumps, patches, cardiac leads, chronic infusion lines, arterial lines, devices for continuous subarachnoid infusions, feeding tubes, CNS shunts (e.g., a ventriculopleural shunt, a VA shunt, or a VP shunt), ventricular peritoneal shunts, ventricular atrial shunts, portosystemic shunts and shunts for ascites.

Further examples of intracorporeal medical devices which can be permanent or temporary are catheters. Examples of catheters include, but are not limited to, central venous catheters, peripheral intravenous catheters, hemodialysis catheters, catheters such as coated catheters include implantable venous catheters, tunnelled venous catheters, coronary catheters useful for angiography, angioplasty, or ultrasound procedures in the heart or in peripheral veins and arteries, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g., chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

Medical devices include endovascular device delivery systems such as stents, occluders, valves, etc., diagnostics catheters containing spectroscopic or imaging capabilities, placement wires, catheters or sheaths.

In a specific embodiment, the surface is the surface of a substrate comprising a medical device selected from the group consisting of stents including bifurcated stents, balloon expandable stents and self-expanding stents, stent-grafts including bifurcated stent-grafts, grafts including vascular grafts and bifurcated grafts, dialators, vascular occluders, embolic filters, embolectomy devices, catheters including microcatheters, central venous catheters, peripheral intravenous catheters and hemodialysis catheters, artificial blood vessels, sheaths including retractable sheaths, blood indwelling monitoring devices, artificial heart valves, pacemaker electrodes, guidewires, cardiac leads, cardiopulmonary bypass circuits, cannulae, plugs, drug delivery devices, balloons, tissue patch devices and blood pumps.

Examples of extracorporeal medical devices are non-implantable devices such as extracorporeal blood treatment devices, and transfusion devices. Devices may have neurological, peripheral, cardiac, orthopedal, dermal and gynecological application, inter alia.

In another embodiment, the above-mentioned stents can be used in cardiac, peripheral or neurological applications. In another embodiment, said stent-grafts can be used in cardiac, peripheral or neurological applications.

In another embodiment, the above-mentioned sheaths can be an interventional diagnostic and therapeutic sheath, large and standard bore endovascular delivery sheaths, arterial introducer sheaths with and without hemostatic control and with or without steering, micro-introducer sheaths, dialysis access sheaths, guiding sheaths, and percutaneous sheaths; all for access in carotid, renal, transradial, transseptal, pediatric and micro applications.

In another embodiment, said medical device can be used in neurological, peripheral, cardiac, orthopedic, dermal, or gynaecologic applications.

Analytical Devices

An analytical device can be, for example, a solid support for carrying out an analytical process such as chromatography or an immunological assay, reactive chemistry or catalysis. Examples of such devices include slides, beads, well plates and membranes.

Separation Devices

A separation device can be, for example, a solid support for carrying out a separation process such as protein purification, affinity chromatography or ion exchange. Examples of such devices include filters, beads, particles, packed beds, arrays, nanoarrays, channels, microfluidics channels, and columns.

The surface to be coated can be the entire surface of the substrate, or only a portion of the surface of the substrate. Certain substrates may have an external surface and an internal surface, either or both of which can be coated. For example, tubular substrates such as artificial blood vessels have an internal surface, or lumen, which can be coated independently from the external surface. A surface comprising an internal and an external surface may only require the internal surface to the coated. Conversely, only the external surface may require the coating. Using the method of the invention, it is possible to apply a different coating to e.g. the external and internal surfaces of the substrate.

In one embodiment, up to 99%, for example up to 95%, 90%, 75%, 50% or 25% of the surface of the substrate is coated with the coating. In one embodiment, both the external and internal surfaces of the substrate are coated. In another embodiment, only the external surface of the substrate is coated. In one embodiment, the substrate to be coated is tubular in shape having an internal surface or lumen, which can be coated independently from the external surface. The surface of the substrate can be porous or non-porous.

Substrate Materials Useful within this Invention

The substrate may comprise or be formed of a metal or a synthetic or naturally occurring organic or inorganic polymer or a ceramic material, inter alia.

Thus, for example, it can be formed from a synthetic or naturally occurring organic or inorganic polymer or material, including but not limited to materials such as polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Non-woven, bioabsorbable web materials comprising a tri-block copolymer such as poly(glycolide-co-trimethylene carbonate) tri-block copolymer (PGA: TMC) are also useful (as described in U.S. Pat. No. 7,659, 219; Biran et al.). Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL. Block copolymer elastomers such as those copolymers having styrene end blocks, and mid-blocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful substrates are polystyrenes, poly(methyl)methacrylates, polyacrylonitriles, poly(vinylacetates), poly(vinyl alcohols), chlorine-containing polymers such as poly(vinyl)chloride, polyoxymethylenes, polycarbonates, polyamides, polyimides, polyurethanes, phenolics, amino-epoxy resins, polyesters, silicones, cellulose-based plastics, and rubber-like plastics.

Combinations of these materials can be employed with and without cross-linking.

Polymeric substrates may optionally be blended with fillers and/or colorants.

In one embodiment, said the substrate is biocompatible and comprises or consists of a polyether-block-amides, such as PEBAX®.

Fluorinated polymers such as fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like, as well as combinations thereof. and combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof may be useful.

Other suitable substrate materials include proteins, such as silk and wool, agarose and alginate. Bio-derived materials, such as cellulose, oxidized cellulose, collagen, gelatin, albumin, elastin, keratin, agar, and the like. Substrates comprising or consisting of fabric are also contemplated. Suitable fabrics may include natural and/or synthetic materials, and may be in woven, non-woven or knitted form, and combinations thereof, and may be selected based on the end use requirements contemplated. Fabrics can be coated with durable water repellent (DWR) or other suitable coatings, again depending on the end use requirements contemplated.

Also, substrates comprising or consisting of certain metals and ceramics can be used in the present invention. Suitable metals include, but are not limited to, biocompatible metals, titanium, stainless steel, high nitrogen stainless steel, gold, silver, rhodium, zinc, platinum, rubidium, copper and magnesium, and combinations thereof. Suitable alloys include cobalt-chromium alloys such as L-605, MP35N, Elgiloy, nickel-titanium alloys (such as Nitinol), tantalum, and niobium alloys, such as Nb-1% Zr, and others. Ceramic substrates include, but are not limited to, silicone oxides, aluminum oxides, alumina, silica, hydroxyapapitites, glasses, calcium oxides, polysilanols, and phosphorous oxide.

In one embodiment, said metal biocompatible and is a nickel-titanium alloy, such as Nitinol.

Coating of the Invention

The present invention relates to the discovery that the problems associated with polydopamine coatings outlined above can, at least in some embodiments, be overcome by the addition of an additive during the coating formation. The additive is a molecule which is functionalised with a photosensitive or thermosensitive moiety and also comprises functionality which enables it to be covalently incorporated within the coating. The resulting coating then comprises photosensitive or thermosensitive groups within the bulk of the coating, which, when activated, form covalent bonds within the coating. As such, at least in some embodiments, the coating of the invention is more durable than a pure polydopamine coating. In some embodiments, the coating of the invention is more stable to sterilisation and to oxidative conditions than a pure polydopamine coating. In some embodiments, the coating of the invention is less susceptible to particulation than a pure polydopamine coating.

The coating of the invention comprises photosensitive or thermosensitive groups on the surface of the coating, as well as within and throughout the bulk of the coating. If the surface being coated has complementary functionality to the photosensitive or thermosensitive groups, then in some embodiments the coating of the invention will be covalently bonded to the surface. For example, if the photosensitive or thermosensitive group is capable of hydrogen abstraction and subsequent covalent bond formation, and if the surface being coated has abstractable hydrogen atoms, then the resulting coating will be covalently bonded to the surface. Likewise, if a subsequent coating which is applied on the surface has complementary functionality to the photosensitive or thermosensitive groups, then in some embodiments the coating of the invention will be covalently bonded to the subsequent coating which is subsequently applied to the surface. In both cases, the durability of the coating can be enhanced. In the latter case, the durability of the subsequent coating can be enhanced.

Component A

Broadly speaking, component A is a polymer which is formed from a monomer which can self-polymerise. In certain embodiments, component A is defined as polymer, while in other embodiments, component A is defined as a monomer which forms said polymer, via self-polymerisation. Thus, in one embodiment, component A is a polymer formed by self-polymerisation of a molecule comprising catechol functionality and amine and/or amide and/or hydroxyl functionality. In another embodiment, component A is a molecule capable of self-polymerisation comprising catechol functionality and amine and/or amide and/or hydroxyl functionality.

"Catechol functionality" refers to any functionality comprising a 1,2-dihydroxybenzene. "Amine functionality" refers to primary amines, secondary amines, tertiary amines and quaternary amines. "Amide functionality" refers to any functionality comprising —NH—(CO)— or —N(R)—CO— groups (wherein R is a substituent other than hydrogen). "Hydroxyl functionality" refers to an —OH group. In one embodiment, component A is a molecule of formula (I):

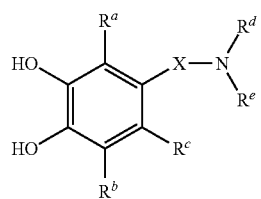

wherein, $R^a$, $R^b$, $R^c$, $R^d$ and $R^e$ are independently selected from the group consisting of H, $C_1$-$C_8$ alkyl, $C_2$-$C_8$ alkenyl, $C_2$-$C_8$alkynyl, —OH, —$CO_2H$, —C(O)—($C_1$-$C_8$ alkyl), —C(O)—($C_2$-$C_8$ alkenyl), —C(O)—($C_2$-$C_8$ alkynyl); and X is $C_1$-$C_8$ alkyl optionally substituted with one or more groups selected from the groups consisting of $C_1$-$C_8$ alkyl, $C_2$-$C_8$ alkenyl, $C_2$-$C_8$ alkynyl, —OH, —$CO_2H$, —C(O)—($C_1$-$C_8$alkyl), —C(O)—($C_2$-$C_8$ alkenyl), —C(O)—($C_2$-$C_8$alkynyl); wherein optionally one or more carbon atoms of the $C_1$-$C_8$ functionality is/are replaced with a group selected from —O—, —S—, —NH—, —N($C_1$-$C_8$ alkyl)-, —NHC(O)— and —N($C_1$-$C_8$ alkyl)C(O)—. Suitably, one or more of $R^a$, $R^b$, $R^c$, $R^d$ and $R^e$ are H.

In one embodiment, component A is a molecule of formula (II):

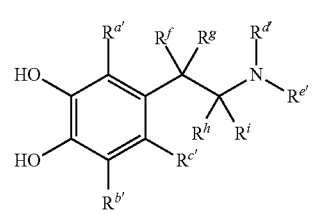

wherein, $R^{a'}$, $R^{b'}$, $R^{c'}$, $R^{d'}$, $R^{e'}$, $R^f$, $R^g$, $R^h$ and $R^i$ are independently selected from the group consisting of: H, $C_1$-$C_8$ alkyl, $C_2$-$C_8$ alkenyl, $C_2$-$C_8$ alkynyl, —OH, —$CO_2H$, —C(O)—($C_1$-$C_8$ alkyl), —C(O)—($C_2$-$C_8$ alkenyl), —C(O)—($C_2$-$C_8$ alkynyl). Suitably, one or more of $R^1$-$R^9$ are not H.

Suitably, component A comprises at least one abstractable hydrogen atom.

In one embodiment, component A is a catecholamine. Catecholamine is a compound that comprises catechol and a side-chain amine.

In one embodiment, component A is dopamine. Dopamine is a catecholamine of formula:

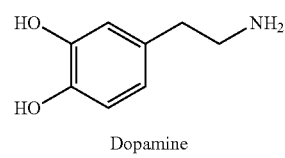 [SMILES: NCCc1ccc(O)c(O)c1]

Dopamine

In another embodiment, component A is a dopamine analogue. Dopamine analogues include molecules involved in the same or similar biochemical pathways as dopamine and/or those that are similar in structure to dopamine, including oxidised derivatives of tyrosine.

Naturally occurring dopamine analogues include:

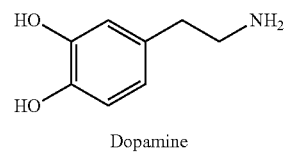

Dopamine

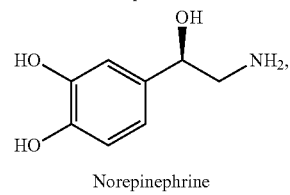

Norepinephrine

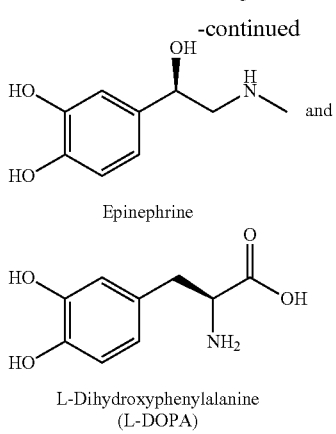

Epinephrine

L-Dihydroxyphenylalanine
(L-DOPA)

In one embodiment, component A is based on melanin. In another embodiment, component A is based on eumelanin.

In embodiments where component A is referred to as being a polymer, rather than a molecule (i.e. a monomer), component A being a polymer of any of the above monomers/molecules is envisaged.

In one embodiment, component A is a polymer formed by self-polymerisation of a molecule comprising catechol functionality and amine and/or amide and/or hydroxyl functionality. In another embodiment, component A is a polymer formed by self-polymerisation of a molecule comprising catechol functionality and amine. In a further embodiment, component A is a polymer formed by self-polymerisation of a catecholamine. Suitably, component A is polydopamine.

In one embodiment, component A is a molecule capable of self-polymerisation comprising catechol functionality and amine and/or amide and/or hydroxyl functionality. In another embodiment, component A is a molecule capable of self-polymerisation comprising catechol functionality and amine functionality. In a further embodiment, component A is a catecholamine capable of self polymerisation. Suitably, component A is dopamine.

The exact structure of polydopamine is not well understood, and a number of structures have been proposed, as illustrated in FIG. 1.

Polymerisation of dopamine occurs under alkaline and oxidative conditions, and mere exposure to the air (i.e. oxygen) is sufficient to initiate polymerisation under alkaline conditions. It is generally acknowledged that the initial oxidation of dopamine occurs on the catechol moiety, which then reacts with another molecule of dopamine, or can undergo an intermolecular cyclisation (via the pendant primary amine) to form a nitrogen-containing bicycle. Structure A of polydopamine (as described in WO2010/006196) suggests that polydopamine consists of repeating 5,6-dihydroxy-3H-indole units, cross-linked through positions 4 and 7. Structure B (as described by Zhao et al. *Polym. Chem.*, 2010, 1, 1430-1433) suggests a similar polymer, but every other 5,6-dihydroxy-3H-indole unit is replaced with a 5,6-dihydroxyindoline unit. Structure C is proposed by the present inventors as another possible structure for polydopamine, which again is similar to Structure A, but every other 5,6-dihydroxy-3H-indole unit is replaced with an un-cyclised dopamine molecule. This structure of polydopamine therefore comprises primary amine functionalities. Structure D (described in Kang et al. *Langmuir*, 2009, 25, 9656-9659) is also proposed by the present inventors and suggests attachment between dopamine molecules at the five-membered nitrogen ring, as well as between the catechol rings. This structure also suggests that quinone rings as well as catechol rings are present in the polymeric structure. Finally, Structure E (described by Dreyer at al. *Langmuir*, 2012, 28, 6428-6435) illustrates a completely different structure in which polydopamine is not a covalent polymer but is instead a supramolecular aggregate of monomers, consisting primarily of 5,6-dihydroxyindoline and its dione derivative. It should be noted that despite the disparity in the proposed structures for polydopamine, all of the structures share the common feature of having a plurality of abstractable hydrogen atoms.

Component A will polymerise in the presence of air, or a source of $O_2$.

Component B

Broadly speaking, component B is a molecule or polymer which comprises photosensitive or thermosensitive moieties and is capable of forming covalent bonds with component A.

Thus, in one embodiment, component B is a cross-linking molecule comprising two or more photosensitive or thermosensitive moieties, at least some of which moieties form covalent bonds with component A.

In another embodiment, component B is a polymer comprising photosensitive or thermosensitive moieties at least some of which moieties form covalent bonds with component A and which polymer forms an interpenetrating network with component A.

In a further embodiment, component B is a mixture of a cross-linking molecule comprising two or more photosensitive or thermosensitive moieties, at least some of which moieties form covalent bonds with component A, and a polymer comprising photosensitive or thermosensitive moieties at least some of which moieties form covalent bonds with component A and which polymer forms an interpenetrating network with component A.

In a further embodiment, component B is a molecule comprising one or more groups capable of participating in the polymerisation of component A, wherein said molecule comprises one or more photosensitive or thermosensitive moieties capable of forming covalent bonds with component A, at least some of which moieties form covalent bonds with component A in the copolymer.

In one embodiment, component B is a monomer. In another embodiment, component B is a polymer.

Photosensitive and Thermosensitive Moieties

Photosensitive moieties are moieties which undergo a change upon exposure to certain wavelengths of light. In one embodiment, the photosensitive moiety undergoes a change upon exposure to UV light. Thermosensitive moieties are moieties which undergo a change on exposure to heat. In the context of the present invention, when photosensitive or thermosensitive moieties are exposed to light or heat respectively, covalent bond formation with component A results.

In one embodiment, component B comprises one or more photosensitive moieties. In another embodiment, component B comprises one or more thermosensitive moieties.

In certain embodiments, the surface to be coated has complementary functionality to the photosensitive or thermosensitive groups, which results in the coating being covalently bonded to the surface.

In certain embodiments, a subsequent coating which is applied on the surface has complementary functionality to the photosensitive or thermosensitive groups, which results in the coating of the invention being covalently bonded to the subsequent coating which is subsequently applied to the surface.

In one embodiment, the photosensitive moiety is a photoinitiator. A photoinitiator is a compound that yields free radicals when exposed to UV or visible light. Based on the mechanism of radical formation, photoinitiators are generally divided into two classes: Type I photoinitiators undergo a unimolecular bond cleavage upon irradiation to yield free radicals. Type II photoinitiators undergo a bimolecular reaction where the excited state of the photoinitiator interacts with a second molecule (a coinitiator, usually a H-donor) to generate free radicals via hydrogen abstraction mechanisms. Subsequent polymerisation is usually initiated by the radicals produced from the coinitiator. UV photoinitiators of both Type I and Type II are available. However, visible light photoinitiators belong almost exclusively to the Type II class of photoinitiators. Thus, in one embodiment, the one or more photosensitive moiety is a Type I or Type II initiator. In another embodiment, the one or more photosensitive moiety is a Type I initiator. In a further embodiment, the one or more photosensitive moiety is a Type II initiator.

In one embodiment, the one or more photosensitive moiety is capable of hydrogen abstraction.

In one embodiment, the one or more photosensitive moiety is an aryl ketone.

In one embodiment, the one or more photosensitive moiety is a diaryl ketone. Suitably, the diaryl ketone is a substituted diaryl ketone. As is known to the art, diaryl ketones tend to react via Type II mechanisms i.e. upon excitation with UV light, the diaryl ketone enters an excited state and can interact with a second molecule via hydrogen abstraction to form a covalent bond with the second molecule via free radical recombination as shown in Scheme 1, infra. In one embodiment, the one or more photosensitive moiety is benzophenone. Suitably, the benzophenone is a substituted benzophenone. Benzophenone may be substituted or functionalised on one phenyl ring or both phenyl rings, in various positions. In one embodiment, the one or more photosensitive moiety is a benzophenone of formula (III):

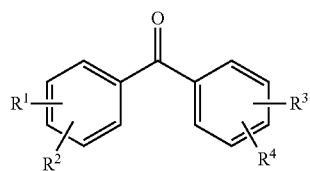

(III)

wherein, $R^1$, $R^2$, $R^3$ and $R^4$ are independently selected from —H, —OH, —$NO_2$, —$CO_2H$, —$CO_2(C_1-C_8$ alkyl), —$O(C_1-C_4$alkyl), —$NH_2$, —$NH(C_1-C_8$ alkyl), —$N(C_1-C_8$ alkyl)$_2$, $C_1-C_8$ alkyl, $C_2-C_8$ alkenyl, $C_2-C_8$ alkynyl, phenyl, —O-phenyl, —S-phenyl, F, Cl, Br and I, or $R^1$ and $R^2$ or $R^3$ and $R^4$ taken together form a cyclic anhydride; wherein $R^1$, $R^2$, $R^3$ and $R^4$ are optionally independently substituted with one or more of —OH, —$NO_2$, —$CO_2H$, —$CO_2(C_1-C_8$ alkyl), —$O(C_1-C_4$ alkyl), —$NH_2$, —$NH(C_1-C_8$ alkyl), —$N(C_1-C_8$ alkyl)$_2$, $C_1-C_8$ alkyl, $C_2-C_8$ alkenyl, $C_2-C_8$ alkynyl, phenyl, —O-phenyl, —S-phenyl, F, Cl, Br or I.

In one embodiment, $R^1$, $R^2$, $R^3$ and $R^4$ are not capable of participating in the polymerisation of component A.

Examples of benzophenone moieties include, but are not limited to, benzophenone, benzophenone-3,3'-4,4'-tetracarboxylic dianhydride, 4-benzoylbiphenyl, 4,4'-bis(diethylamino)benzophenone, 4,4'-bis[2-(1-propenyl)phenoxy]benzophenone, 4-(diethylamino)benzophenone, 4,4'-dihydroxybenzophenone, 4-(dimethylamino)benzophenone, 3,4-dimethylbenzophenone, 4-aminobenzophenone, 4,4'-diaminobenzophenone, 3-hydroxybenzophenone, 4-hydroxybenzophenone, 4,4'-dihydroxybenzophenone, 3,4-diaminobenzophenone, 2-methylbenzophenone, 3-methylbenzophenone, 4-methylbenzophenone, and Michler's ketone.

The benzophenone can form part of component B by attachment (at one or more points) via one phenyl ring or both phenyl rings. Alternatively, component B may be the benzophenone molecule itself.

In one embodiment, component B comprises or consists of a polymeric initiator. Polymer initiators comprise a polymer backbone and multiple pendant initiator groups. For example, a polymeric initiator can comprise multiple diaryl ketone, e.g. benzophenone moieties (polybenzophenone). Thus, in one embodiment, component B comprises, or consists of, a polydiaryl ketone, e.g. polybenzophenone. Omnipol and Omnirad are trade names for a class of polybenzopheones comprising poly(alkylene glycol)-dibenzophenone.

In one embodiment, the photosensitive moiety is phthalimide.

In one embodiment, the photosensitive moiety is an aryl azide, for example an aryl azide of formula (IV):

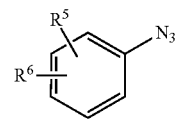

(IV)

wherein, $R^5$ and $R^6$ are independently selected from the group consisting of —H, —OH, —$NO_2$, —$CO_2H$, —$CO_2(C_1-C_8$ alkyl), —$O(C_1-C_4$ alkyl), —$NH_2$, —$NH(C_1-C_8$ alkyl), —$N(C_1-C_8$ alkyl)$_2$, $C_1-C_8$ alkyl, $C_2-C_8$ alkenyl, $C_2-C_8$ alkynyl, phenyl, —O-phenyl, —S-phenyl, F, Cl, Br and I; wherein $R^5$ and $R^6$ are optionally independently substituted with one or more of —OH, —$NO_2$, —$CO_2H$, —$CO_2(C_1-C_8$ alkyl), —$O(C_1-C_4$alkyl), —$NH_2$, —$NH(C_1-C_8$ alkyl), —$N(C_1-C_8$ alkyl)$_2$, $C_1-C_8$ alkyl, $C_2-C_8$ alkenyl, $C_2-C_8$ alkynyl, phenyl, —O-phenyl, —S-phenyl, F, Cl, Br and I.

In one embodiment, $R^5$ and $R^6$ are not capable of participating in the polymerisation of component A.

The aryl azide can form part of component B via attachment (at one or more points) via the phenyl ring. Alternatively, component B may be the aryl azide itself.

In one embodiment, the photosensitive moiety is a diazirine, for example a diazirine of formula (V):

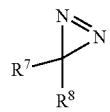

(V)

wherein, both $R^7$ and $R^8$ are points of attachment via which the diazirine forms part of component B, or one of $R^7$ and $R^8$ is a point of attachment via which the diazirine forms part of component B, and the remaining $R^7$ or $R^8$ is selected from the group consisting of H and $C_1-C_8$ alkyl.

In an alternative embodiment, $R^7$ and $R^8$ are independently selected from the group consisting of H, $C_1-C_8$ alkyl, —($C_1-C_8$ alkyl)-$CO_2$-(succinimide), —($C_1-C_8$ alkyl)-C(O)NH—($C_1-C_8$ alkyl)-(succinimide) and —($C_1-C_8$ alkyl)-C (O)NH—($C_1$-$C_8$ alkyl)-S—S—($C_1$-$C_8$ alkyl)-(succinimide), wherein succinimide is optionally substituted with —$SO_3$Na. In this embodiment, component B is the diazirine molecule itself.

In one embodiment, the photosensitive moiety is a furocoumarin, for example psoralen.

In one embodiment, the photosensitive moiety is $C_2$-$C_8$ alkenyl or $C_2$-$C_8$ alkynyl.

In one embodiment, the one or more photosensitive moieties are selected from the group consisting of aryl ketone, diaryl ketone, aryl azide, alkenyl and alkynyl. In another embodiment, the one more photosensitive moiety is a diaryl ketone or alkenyl. In a further embodiment, the one or more photosensitive moiety is benzophenone or $C_2$-$C_8$ alkenyl.

Reactivity of Photosensitive and Thermosensitive Moieties

The photosensitive or thermosensitive moieties of component B, when activated, will react in such a way so as to form a covalent bond with component A.

In one embodiment, the photosensitive or thermosensitive moiety, once activated, is capable of hydrogen abstraction. For example, diaryl ketones such as benzophenone can react via a Type II reaction mechanism to abstract hydrogen atoms. A representative reaction scheme of the activation of a component B which comprises benzophenone is illustrated in Scheme 1 below:

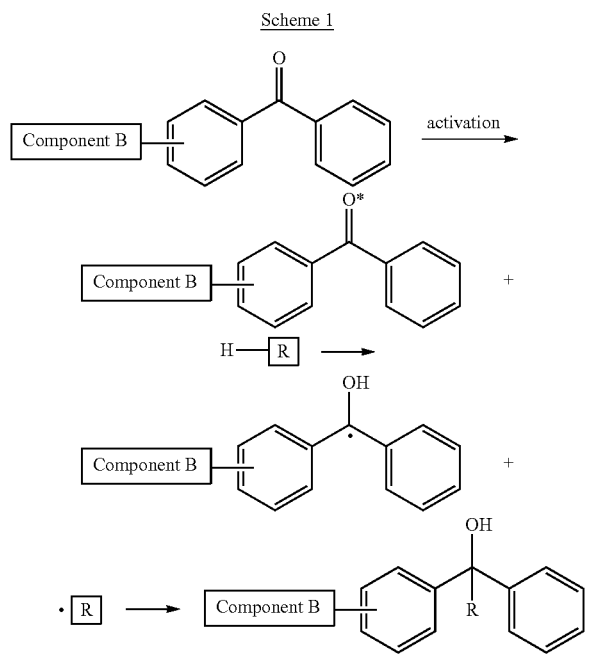

Scheme 1

As shown in Scheme 1, when exposed to UV light the triplet excited state of benzophenone is formed, which can abstract a hydrogen from another molecule (represented as H—R) to form a ketyl radical and a radical R'. The radical intermediate then collapses to form a covalent bond between the benzophenone molecule and molecule R. Thus, component B and R are covalently bonded. The H-abstraction mechanism illustrated in Scheme 1 is a widely known photochemical mechanism which has utility in grafting processes.

H—R in Scheme 1 represents component A. In some embodiments, H—R also represents the surface to be coated.

In this embodiment, the resulting coating is covalently bonded to the surface. In some embodiments, H—R also represents a subsequent coating which is applied on the surface. In this embodiment, the coating of the invention is covalently bonded to the subsequent coating.

Certain photosensitive or thermosensitive moieties, once activated, form carbenes or nitrenes. Thus, in one embodiment, component B comprises one or more photosensitive or thermosensitive moieties capable of forming a carbene or nitrene. A carbene is a molecule containing a neutral carbon atom with a valence of two and two unshared valence electrons, of general formula R—(C:)—R' or R=C:. Alternatively, a carbene can be defined as a molecule containing a carbon atom with an unpaired free electron i.e. a free radical. A nitrene is a nitrogen analogue of a carbene. Carbenes and nitrenes can initiate addition reactions with double bonds and undergo insertion into C—H and N—H bonds, leading to covalent bond formation and in some cases ring expansion.

Groups Capable of Participating in Catecholamine Polymerisation

In one embodiment, component B comprises one or more groups capable of participating in the polymerisation of component A. In this embodiment, when components A and B are mixed in solution, they will polymerise to form a co-polymer of components A and B.

In one embodiment, the one or more groups capable of participating in polymerisation of component A are independently selected from the group consisting of amino, hydroxyl, catechol, thiol, hydrazine, hydrazone, oxime, keto, aldehyde, carboxyl, imino, amido, alkenyl (such as $C_2$-$C_8$ alkenyl) and alkynyl (such as $C_2$-$C_8$ alkynyl). Suitably, the one of the one or more groups capable of participating in the polymerisation of component A are selected from the group consisting of amino, hydroxyl, catechol, amido and $C_2$-$C_8$ alkenyl.

Examples of Component B

In one embodiment, component B is of formula (VI), formula (VII), formula (VIII), formula (IX), formula (X) or formula (XI):

 (VI)

 (VII)

 (VIII)

 (IX)

 (X)

 (XI)

wherein,
each Z is independently a photosensitive or thermosensitive group, as described above;
each X is a moiety comprising a functional group capable of participating in the polymerisation of component A; and each Y is independently selected from the group consisting of a covalent bond, $C_1$-$C_8$ alkyl, $C_2$-$C_8$ alkenyl, $C_2$-$C_8$ alkynyl, —(CH$_2$CH$_2$O)$_{1-20}$—, —C(O)—NH—($C_1$-$C_8$ alkyl)-, —NH—C(O)—($C_1$-$C_8$ alkyl)-, —C(O)—NH—($C_1$-$C_8$ alkyl)-NH—C(O)—, —NH—C(O)—($C_1$-$C_8$ alkyl)-C(O)—NH—, —NH—$C_1$-$C_8$ alkyl-NH(CO)—, —N($C_1$-$C_8$ alkyl-NH(CO)—)$_2$, N($C_1$-$C_8$ alkyl-NH(CO)—)$_3$, phenyl and —($C_1$-$C_8$ alkyl)-phenyl; wherein, each Y is optionally independently substituted with $C_1$-$C_8$ alkyl, $C_2$-$C_8$ alkenyl or —O($C_1$-$C_8$ alkyl);

q is 1-4;

r is 1-4;

m is 1-5000; and n is 1-100; wherein the ratio of m:n is from about 1:1 to about 1:0.02.

In one embodiment, each Z is independently selected from the group consisting of benzophenone and $C_2$-$C_8$ alkenyl. Suitably each Z is benzophenone, such as a benzophenone of formula (III).

In one embodiment, each X is independently selected from the group consisting of amino, hydroxyl, catechol, thiol, hydrazine, hydrazone, oxime, keto, aldehyde, carboxyl, imino, amido, $C_2$-$C_8$ alkenyl and $C_2$-$C_8$ alkynyl. Suitably, each X is selected from the group consisting of amino, hydroxyl, catechol, amido and $C_2$-$C_8$ alkenyl.

In one embodiment, each Y is independently selected from the group consisting of a covalent bond, $C_1$-$C_8$ alkyl, $C_2$-$C_8$ alkenyl, —(CH$_2$CH$_2$O)$_{1-20}$—, —C(O)—NH—($C_1$-$C_8$ alkyl)-, —NH—C(O)—($C_1$-$C_8$ alkyl)-, C(O)—NH—($C_1$-$C_8$ alkyl)-NH—(C(O)— and phenyl; wherein each Y is optionally independently substituted with $C_1$-$C_8$ alkyl, $C_2$-$C_8$ alkenyl or —O($C_1$-$C_8$ alkyl).

In one embodiment, q is 1-3, 1-2, 4, 3, 2 or 1.

In one embodiment, r is 1-3, 1-2, 4, 3, 2 or 1.

In one embodiment, m is 1-4500, for example 100-4000 or 1000-3000.

In one embodiment, n is 10-100, for example 10-80, 20-80 or 50-80.

In one embodiment, ratio of m:n is from about 1:1 to about 1:0.05, for example 1:1 to about 1:0.1, for example 1:1 to about 1:0.5.

Formula (VI)

In one embodiment, component B is of formula (VI):

$$Z\text{---}[\text{---}Y\text{---}X]_q \quad (VI)$$

wherein Z, X, Y and q are as defined above.

In one embodiment, component B is of formula (VI) wherein Z is benzophenone or $C_2$-$C_8$ alkenyl; each Y is independently selected from the group consisting of a covalent bond, $C_1$-$C_8$ alkyl, $C_2$-$C_8$ alkenyl, —(CH$_2$CH$_2$O)$_{1-20}$—, —C(O)—NH—($C_1$-$C_8$ alkyl)-, —NH—C(O)—($C_1$-$C_8$ alkyl)-, —C(O)—NH—($C_1$-$C_8$ alkyl)-NH—C(O)—, or —NH—C(O)—($C_1$-$C_8$ alkyl)-C(O)—NH—, phenyl and —($C_1$-$C_8$ alkyl)-phenyl; wherein each Y is optionally independently substituted with $C_1$-$C_8$ alkyl, $C_2$-$C_8$ alkenyl or —O($C_1$-$C_8$ alkyl); X is selected from the group consisting of amino, hydroxyl, catechol, thiol, hydrazine, hydrazone, oxime, keto, aldehyde, carboxyl, imino, amido, $C_2$-$C_8$ alkenyl and $C_2$-$C_8$ alkynyl; and q is 1-4.

In one embodiment, component B is of formula (VI), wherein Z is a benzophenone of formula (III) or $C_2$-$C_8$ alkenyl; Y is a covalent bond, $C_1$-$C_8$ alkyl, $C_2$-$C_8$ alkenyl, —(CH$_2$CH$_2$O)$_{1-20}$—, —C(O)—NH—($C_1$-$C_8$ alkyl)-, —NH—C(O)—($C_1$-$C_8$ alkyl)-, —C(O)—NH—($C_1$-$C_8$ alkyl)-NH—C(O)—, or —NH—C(O)—($C_1$-$C_8$ alkyl)-C(O)—NH—, phenyl or —($C_1$-$C_8$ alkyl)-phenyl, wherein each Y is optionally independently substituted with $C_1$-$C_8$ alkyl, $C_2$-$C_8$ alkenyl or —O($C_1$-$C_8$ alkyl); X is selected from the group consisting of amino, hydroxyl, catechol, thiol, hydrazine, hydrazone, oxime, keto, aldehyde, carboxyl, imino, amido, $C_2$-$C_8$ alkenyl and $C_2$-$C_8$ alkynyl; and q is 1-4.

In another embodiment, component B is of formula (VI), wherein Z is a benzophenone of formula (III) or $C_2$-$C_8$ alkenyl; Y is a covalent bond or —($C_1$-$C_8$ alkyl)-phenyl, wherein each Y is optionally independently substituted with $C_1$-$C_8$ alkyl, $C_2$-$C_8$ alkenyl or —O($C_1$-$C_8$ alkyl); X is selected from the group consisting of amino, hydroxyl, $C_2$-$C_8$ alkenyl and catechol; and q is 1-4, suitably 1-2.

In one embodiment, component B is selected from the group consisting of:

dopamine benzoyl benzamide ("dopa-BBA"; see Example 2a)

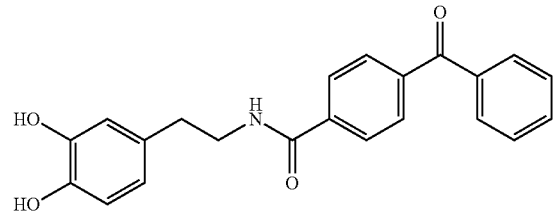 [SMILES: O=C(NCCc1ccc(O)c(O)c1)c1ccc(C(=O)c2ccccc2)cc1]

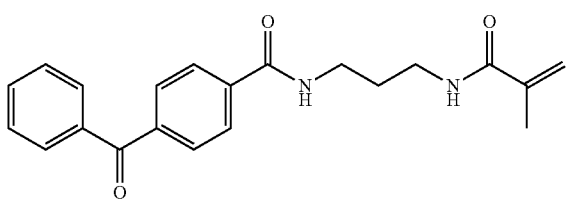

3-amido(4-benzoylbenzoyl)propyl methacrylamide ("ABBPMA"; see Example 2c)

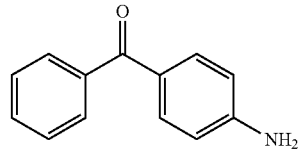

4-aminobenzophenone

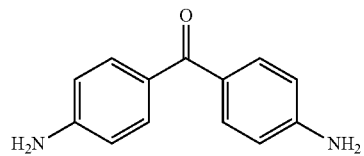

4,4'-diaminobenzophenone

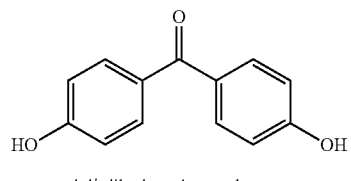

4,4'-dihydroxybenzophenone

[Structure: 3,4-diaminobenzopheneone]

[Structure: eugenol]

In one embodiment, component B is dopamine benzoyl benzamide.

Formula VII

In one embodiment, component B is of formula (VII):

$$[Z]_r Y \quad (VII)$$

wherein, Z, Y and r are as defined above.

In one embodiment, component B is of formula (VII) wherein Z is a benzophenone of formula (III) or $C_2$-$C_8$ alkenyl; Y is selected from the group consisting of $C_1$-$C_8$ alkyl, $C_2$-$C_8$ alkenyl, $C_2$-$C_8$ alkynyl, —(CH$_2$CH$_2$O)$_{1-20}$—, —C(O)—NH—($C_1$-$C_8$ alkyl)-, —NH—C(O)—($C_1$-$C_8$ alkyl)-, —C(O)—NH—($C_1$-$C_8$ alkyl)-NH—C(O)—, —NH—C(O)—($C_1$-$C_8$ alkyl)-C(O)—NH—, —NH—$C_1$-$C_8$ alkyl-NH(CO)—, —N($C_1$-$C_8$ alkyl-NH(CO)—)$_2$, N($C_1$-$C_8$ alkyl-NH(CO)—)$_3$, phenyl and —($C_1$-$C_8$ alkyl)-phenyl; and r is 1-4.

In another embodiment, component B is of formula (VII) wherein Z is a benzophenone of formula (III), Y is N($C_1$-$C_8$ alkyl-NH(CO)—)$_3$; and r is 3.

In one embodiment, component B is tris-[amino(ethyl-benzoylbenzamide)] ("tris-BBA"; synthesis described in Example 2b)

[Structure: tris-BBA]

In one embodiment, component B is of formula (VII) wherein, Z and Y are as previously defined and r is 2. In this embodiment, component B forms cross-linkages within component A.

Formula (VIII)

In one embodiment, component B is of formula (VIII):

$$X-Y-Z-Y-X \quad (VIII)$$

wherein, X, Y and Z are as defined above.

Formula (IX)

In one embodiment, component B is of formula (IX):

$$\left[\begin{array}{c}Y\\|\\X\end{array}\right]_m \left[\begin{array}{c}Y\\|\\Z\end{array}\right]_n \quad (IX)$$

wherein, X, Y, Z, m and n are as defined above.

In one embodiment, component B is of formula (IX) wherein Z is a photosensitive group as described above; each X is a moiety comprising a functional group capable of participating in the polymerisation of component A; and each Y is independently selected from the group consisting of a covalent bond, $C_1$-$C_8$ alkyl, $C_2$-$C_8$ alkenyl and $C_2$-$C_8$ alkynyl, wherein each Y is optionally independently substituted with $C_1$-$C_8$ alkyl, $C_2$-$C_8$ alkenyl or —O($C_1$-$C_8$ alkyl); m is 1-5000; and n is 1-100.

In another embodiment, component B is of formula (IX) wherein Z is a benzophenone, X is a moiety comprising an amide moiety, and is suitably pyrrolidone; each Y is $C_1$-$C_8$ alkyl, optionally substituted with $C_1$-$C_8$ alkyl; m is 100-4000; and n is 10-80.

In one embodiment, component B is poly(vinylpyrrolidone-co-amido(4-benzoylbenzoyl)propyl methacrylate ("VP-co-BBA"; see Example 2d)

[Structure: VP-co-BBA copolymer]

Formula (X)

In one embodiment, component B is of formula (X):

$$\left[\begin{array}{c}X\\|\\Y\\|\\Z\end{array}\right]_m \quad (X)$$

wherein, X, Y, Z and m are as defined above.

Formula (XI)

In one embodiment, component B is of formula (XI):

$$\left[\begin{array}{c}Y\\|\\Z\end{array}\right]_m \quad (XI)$$

wherein, Y, Z and m are as defined above.

Further Examples of Component B

In one embodiment, component B is of formula (XII):

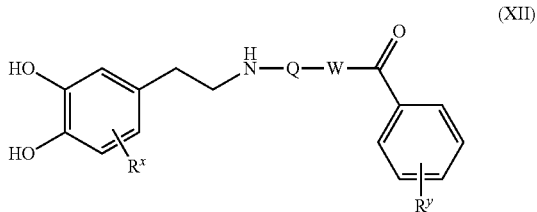

wherein, $R^x$ is selected from the group consisting of —H, —OH, —NO$_2$, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, C$_1$-C$_8$ alkyl, C$_2$-C$_8$ alkenyl, C$_2$-C$_8$ alkynyl, phenyl, —O-phenyl, —S-phenyl; $R^y$ is selected from the group consisting of —H, —OH, —NO$_2$, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, C$_1$-C$_8$ alkyl, C$_2$-C$_8$ alkenyl, C$_2$-C$_8$ alkynyl, phenyl, —O-phenyl, —S-phenyl, wherein $R^x$ and $R^y$ are optionally independently substituted with one or more of —OH, —NO$_2$, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, C$_1$-C$_8$ alkyl, C$_2$-C$_8$ alkenyl, C$_2$-C$_8$ alkynyl, phenyl, —O-phenyl or —S-phenyl; Q is selected from the group consisting of a covalent bond, C$_1$-C$_8$ alkyl, C$_2$-C$_8$ alkenyl and —C(O)—(C$_1$-C$_8$ alkyl)-; and W is a covalent bond or phenyl, wherein phenyl is optionally substituted with one or more R.

In one embodiment, component B is of formula (XII), wherein $R^x$ is selected from the group consisting of —H, —OH, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, and C$_1$-C$_8$ alkyl.

In one embodiment, $R^y$ is selected from the group consisting of —H, —OH, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, C$_1$-C$_8$ alkyl, C$_2$-C$_8$ alkenyl, and phenyl.

In one embodiment, $R^x$ and $R^y$ are optionally independently substituted with one or more of —OH, —NO$_2$, —CO$_2$H, —CO$_2$(C$_1$-C$_8$ alkyl), —O(C$_1$-C$_4$alkyl), —NH$_2$, —NH(C$_1$-C$_8$ alkyl), —N(C$_1$-C$_8$ alkyl)$_2$, or C$_1$-C$_8$ alkyl.

In one embodiment, Q is selected from the group consisting of a covalent bond, C$_2$-C$_4$ alkyl, C$_2$-C$_8$ alkenyl and —C(O)—(C$_1$-C$_4$ alkyl)-.

In one embodiment, W is a covalent bond.

In one embodiment, component B is selected from the group consisting of dopamine benzoyl benzamide ("dopa-BBA"), 3-amido(4-benzoylbenzoyl)propyl methacrylamide ("ABBPMA"), tris-[amino(ethylbenzoylbenzamide)] ("tris-BBA"), 4-aminobenzophenone, eugenol, 4,4'-diaminobenzophenone, 4,4'-dihydroxybenzophenone, 3,4-diaminobenzopheneone and a polymeric photoinitiator such as a polydiaryl ketone e.g. a polybenzophenone.

In one embodiment, component B has molecular weight of 1-1000 kDa, such as 1-500 kDa, 20-450 kDa or 50-400 kDa.

In one aspect, the present invention provides a surface having a coating comprising a mixture of components A and B, wherein
component A is a polymer formed by self-polymerisation of a molecule comprising catechol functionality and amine and/or amide and/or hydroxyl functionality; and
component B is a cross-linking molecule comprising two or more photosensitive or thermosensitive moieties, at least some of which moieties form covalent bonds with component A.

In another aspect, the present invention provides a surface having a coating comprising a mixture of components A and B, wherein
component A is a polymer formed by self-polymerisation of a molecule comprising catechol functionality and amine and/or amide and/or hydroxyl functionality; and
component B is a polymer comprising photosensitive or thermosensitive moieties at least some of which moieties form covalent bonds with component A and which polymer forms an interpenetrating network with component A.

In a further aspect, the present invention provides a surface having a coating comprising A a mixture of components A and B, wherein
component A is a polymer formed by self-polymerisation of a molecule comprising catechol functionality and amine and/or amide and/or hydroxyl functionality; and
component B is a mixture of;
(iii) a cross-linking molecule comprising two or more photosensitive or thermosensitive moieties, at least some of which moieties form covalent bonds with component A; and
(iv) a polymer comprising photosensitive or thermosensitive moieties at least some of which moieties form covalent bonds with component A and which polymer forms an interpenetrating network with component A.

In one aspect, the present invention provides a surface having a coating comprising a cross-linked copolymer of components A and B, wherein
component A is a catecholamine capable of self-polymerisation; and
component B is a molecule comprising one or more groups selected from the group consisting of amino, hydroxyl, catechol, thiol, hydrazine, hydrazone, oxime, keto, aldehyde, carboxyl, imino, amido, alkenyl and alkynyl, wherein said molecule also comprises one or more photosensitive moieties selected from the group consisting of aryl ketone, diaryl ketone, aryl azide, alkenyl and alkynyl.

In one aspect, the present invention provides a surface having a coating comprising a cross-linked copolymer of components A and B, wherein
component A is a catecholamine capable of self-polymerisation; and
component B is a molecule comprising one or more groups selected from the group consisting of amino, hydroxyl, amido and alkenyl, wherein said molecule also comprises one or more benzophenone groups.

In one embodiment, the coating comprises catecholamine and benzophenone throughout its bulk.

Methods of the Invention

The present invention provides a method of coating a surface, for which there are three main embodiments 1a, 1b and 2, depending on the nature of component B. It should be noted that all embodiments relating to components A and B described above with reference to the surface having a coating of the invention also apply to the methods of the invention.

Embodiments 1a and 1b

In one aspect of the invention is provided a method of coating a surface, comprising the steps of:
(a) contacting the surface with a mixture comprising components A and B, wherein component A is a molecule capable of self-polymerisation comprising catechol functionality and amine and/or amide and/or hydroxyl functionality; and component B is
(i) a cross-linking molecule comprising two or more photosensitive or thermosensitive moieties capable of forming covalent bonds with component A; or
(ii) a polymer comprising photosensitive or thermosensitive moieties capable of forming covalent bonds with component A;
such that component A self-polymerises in the presence of component B and in the case of (ii) forms an interpenetrating network with component B; and
(b) activating the photosensitive or thermosensitive moieties of component B such that at least some of said moieties form covalent bonds with component A.

In Embodiment 1a, component B is a cross-linking molecule comprising two or more photosensitive or thermosensitive moieties capable of forming covalent bonds with component A. Embodiment 1a is illustrated in FIG. 2, which shows that when components A and B are mixed together in step (a), component A polymerises in solution but component B does not. In step (b), once activated, component B forms covalent bonds to component A and forms cross-linkages within the bulk of component A because it is functionalised with two photosensitive or thermosensitive moieties.

An example of a component B which is suitable for Embodiment 1a is a compound of formula (VII) wherein, Z and Y are as previously defined and r is 2.

In Embodiment 1b, component B is a polymer comprising photosensitive or thermosensitive moieties capable of forming covalent bonds with component A; and when component A self-polymerises in the presence of component B, component A forms an interpenetrating network with component B. Embodiment 1b is illustrated in FIG. 3, which shows that when components A and B are mixed together in step (a) component A polymerises in solution and entanglement with component B (which is also a polymer) results. In step (b), upon activation, component B forms covalent bonds to component A, to produce a cross-linked polymer of components A and B.

An example of a component B which is suitable for embodiment 1b is a compound of formula (XI):

(XI)

wherein, Y, Z and m are as defined above.

Embodiment 2

In another aspect of the invention is provided a method of coating a surface comprising the steps of:
(a) contacting the surface with a mixture comprising components A and B, wherein
component A is a molecule capable of self-polymerisation comprising catechol functionality and amine and/or hydroxyl functionality; and
component B is a molecule comprising one or more groups capable of participating in the polymerisation of component A, wherein said molecule comprises one or more photosensitive or thermosensitive moieties capable of forming covalent bonds with component A such that a copolymer of components A and B is formed; and (b) activating the photosensitive or thermosensitive moieties of component B in the copolymer such that at least some of said moieties form covalent bonds with component A.

In Embodiment 2, component B is a molecule comprising one or more groups capable of participating in the polymerisation of component A, wherein said molecule comprises one or more photosensitive or thermosensitive moieties capable of forming covalent bonds with component A such that a copolymer of components A and B is formed. Embodiment 2 is illustrated in FIG. 4, which shows that when components A and B are mixed together in step (a), components A and B will polymerise to form a copolymer. In step (b), upon activation, component B forms covalent bonds to component A, resulting in a cross-linked copolymer of components A and B.

Examples of suitable molecules which are suitable for Embodiment 2, but are not limited to, compounds of formula (VI), (VIII), (IX), (X):

(VI)

(VIII)

(IX)

(X)

wherein, Z, Y, X, m and n are as defined above.

Activation of Photosensitive and Thermosensitive Moieties

In step (b), activation of the one or more photosensitive or thermosensitive moieties of component B results in at least some of the component B moieties forming covalent bonds with component A. Photosensitive moieties, for example aryl ketones, are activated on exposure to particular wavelengths of light. In one embodiment, the one or more photosensitive moieties are activated by exposure of the coated surface to UV light. Thermosensitive moieties, for example aryl azides, are activated on exposure to heat. In one embodiment, component B comprises one or more moieties which are both photosensitive and thermosensitive.

Particular Embodiments of the Method of the Invention

In one aspect, the present invention provides a method of coating a surface, comprising the steps of:
(a) contacting the surface with a mixture comprising components A and B, wherein
component A is a molecule capable of self-polymerisation comprising catechol functionality and amine and/or amide and/or hydroxyl functionality; and
component B is a cross-linking molecule comprising two or more photosensitive or thermosensitive moieties capable of forming covalent bonds with component A;
such that component A self-polymerises in the presence of component B and in the case of (ii) forms an interpenetrating network with component B; and
(b) activating the photosensitive or thermosensitive moieties of component B such that at least some of said moieties form covalent bonds with component A.

In another aspect, the present invention provides a method of coating a surface, comprising the steps of:
(a) contacting the surface with a mixture comprising components A and B, wherein
component A is a molecule capable of self-polymerisation comprising catechol functionality and amine and/or amide and/or hydroxyl functionality; and
component B is a polymer comprising photosensitive or thermosensitive moieties capable of forming covalent bonds with component A;
such that component A self-polymerises in the presence of component B and forms an interpenetrating network with component B; and
(b) activating the photosensitive or thermosensitive moieties of component B such that at least some of said moieties form covalent bonds with component A.

A method of coating a surface, comprising the steps of:
(a) contacting the surface with a mixture comprising components A and B, wherein
component A is a molecule capable of self-polymerisation comprising catechol functionality and amine and/or amide and/or hydroxyl functionality; and
component B is a mixture of
(i) a cross-linking molecule comprising two or more photosensitive or thermosensitive moieties capable of forming covalent bonds with component A; and
(ii) a polymer comprising photosensitive or thermosensitive moieties capable of forming covalent bonds with component A;
such that component A self-polymerises in the presence of component B and forms an interpenetrating network with component B; and
(b) activating the photosensitive or thermosensitive moieties of component B such that at least some of said moieties form covalent bonds with component A.

In one aspect, the present invention provides a method of coating a surface, comprising the steps of:
(a) contacting the surface with a mixture comprising components A and B, wherein
component A is a catecholamine capable of self-polymerisation; and
component B is a molecule comprising one or more groups selected from the group consisting of amino, hydroxyl, catechol, thiol, hydrazine, hydrazone, oxime, keto, aldehyde, carboxyl, imino, amido, alkenyl and alkynyl, wherein said molecule also comprises one or more photosensitive moieties selected from the group consisting of aryl ketone, diaryl ketone, aryl azide, alkenyl and alkynyl; such that a copolymer of components A and B is formed; and
(b) activating the photosensitive moieties of component B in the copolymer such that at least some of said moieties form covalent bonds with component A.

Properties of the Coating

The coating of the invention comprises components A and B, wherein component B is an additive molecule which is functionalised with a photosensitive or thermosensitive moiety and also comprises functionality which enables it to be covalently bonded to component A.

As shown in Examples the addition of component B enhances the durability of the coating and prevents depolymerisation of the coating under oxidative conditions (such as on exposure to peroxide, chlorite or hypochlorite). As described in Example 3, Pebax/BaSO$_4$ tubing was contacted with mixtures of various compounds comprising a photosensitive moiety (as component B) and dopamine (as component A), to form a coating of a copolymer of components A and B (step (a); Embodiment 2, as described above). The coated tubing was then activated/cured as described in Example 4, by exposing the coating to UV light. It is clear from comparing Tables 1 and 2 of Example 5 that coatings which underwent UV curing (i.e. step (b)) were more resistant to oxidative conditions that those which did not, as evidenced by the fact that coatings which underwent UV curing (step (b)) retained their coating colouration, while those coatings which did not undergo UV curing lost colouration, indicating degradation and erosion of the coating.

During this experiment it was observed that coatings of the invention had various colours ranging from dark grey, dark brown, brown yellow, yellow brown, yellow orange and yellow. The coating were observed to retain their colouration over time. This is surprising, since the prior art teaches that dopamine polymerisation solutions become grey or black during dopamine polymerization, and produce grey or black, rather than coloured, coatings (E Herlinger, J Chem Soc Perkin Trans, vol. 2, p. 259, 1995). In one embodiment, the coating of the invention reflects electromagnetic radiation of red to yellow wavelengths.

As discussed above, the coating of the invention is durable and resistant to degradation, erosion and depolymerisation under oxidative conditions such as peroxide, chlorite and hypochlorite. Thus, in one embodiment, the coating of the invention does not appreciatively depolymerise under oxidative conditions, such as exposure to a chlorite compound. In another embodiment, the coating of the invention comprising components A and B is more durable than the corresponding coating consisting solely of component A.

As shown in Examples 6 and 7, the coating of the invention was applied to many different surfaces, all of which were found to be resistant to oxidative depolymerisation.

Covalent Bonding to the Surface

As the coating of the invention comprises photosensitive or thermosensitive groups on the surface of the coating as well as within the bulk of the coating, if the surface being coated has complementary functionality to the photosensitive or thermosensitive groups, then in some embodiments the coating of the invention will be covalently bonded to the surface. FIG. 5 illustrates a variant of Embodiment 2, wherein the surface being coated has complementary functionality (CZ) to the photosensitive or thermosensitive group of component B (Z). Upon activation of group Z, component B will form covalent bonds with component A to form cross-linkages within the bulk of the coating, and Z groups which are in proximity to the surface will form covalent bonds with the surface. It should be noted that the above also applies to Embodiments 1a and 1b. This variant of the coating of the invention is expected to be particularly durable because of the cross-linking within the coating and because of the covalent bonding to the surface. In some embodiments, component A is also capable of reacting with the surface.

For example, if the photosensitive or thermosensitive moiety is capable of hydrogen abstraction and subsequent covalent bond formation, and if the surface being coated has abstractable hydrogen atoms, then the resulting coating will be covalently bonded to the surface. Alternatively, the photosensitive or thermosensitive moiety, once activated, could generate a nitrene or carbene. Suitable complementary reactive groups for nitrenes and carbenes include, but are not limited to, alkyl, alkenyl and alkynyl.

Thus, in one embodiment, the coating of the invention is covalently bonded to the surface. In another embodiment, the surface comprises abstractable hydrogen atoms and the coating is covalently bonded to the surface via abstraction of hydrogen atoms from the surface by at least some of the photosensitive or thermosensitive moieties of component B.

The surface may have "intrinsic" complementary functionality (CZ) to the photosensitive or thermosensitive group of component B (Z), meaning the material from which the surface is made (prior to any coating process) comprises the complementary functionality. Alternatively, the surface may be pre-treated to place a population of CZ, e.g. a surface treatment such as plasma, corona, heat treatment, ozonation, silanizing, ion implantation, surfactant adsorption, etc. (as per below).

In one embodiment, the surface to be coated comprises abstractable hydrogen atoms.

"Abstractable hydrogen atoms" are defined as covalently bound hydrogen atoms that can be abstracted or removed by an entity, being in an excited state, and thereby generating a free radical (at least initially) at the atom which was previously covalently bound to the hydrogen atom (see Scheme 1, supra).

Examples of surface materials having an intrinsic surface comprising abstractable hydrogen atoms include, but are not limited to aliphatic polymers, vinyl polymers, condensation polymers; fluorinated copolymers (although not perfluoropolymers), silanated metals and ceramics, biopolymers.

Surfaces lacking such complementary functionality can be covered, at least in part, with a polymeric covering material having a multiplicity of reactive chemical groups thereon to which said component B (and optionally component A) can react. Polymeric substrates can also be modified along their surface, or along their polymer backbone using a variety of methods, including hydrolysis, aminolysis, photolysis, etching, plasma modification, plasma polymerization, carbene insertion, nitrene insertion, etc. In the resulting coatings of the invention, component B (and optionally component A) are covalently attached, or bound, to the polymeric covering material through the reactive chemical groups of the covering material or directly to a substrate that has been modified. The polymeric covering material may form at least one layer on at least a portion of a substrate. Thus, in one embodiment, prior to applying the coating of the invention the surface is coated with a polymeric covering material comprising complementary functionality.

Subsequent Coatings

The coating of the invention is suitably a priming coating upon which subsequent coatings may be applied. Thus, in one embodiment, the surface has a subsequent coating. In another embodiment, the method of the invention further comprises the step of (c) applying a subsequent coating to the surface.

Subsequent coatings that can be applied to the surface include, but are not limited to a synthetic or naturally occurring organic or inorganic polymer or material, including but not limited to materials such as polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Nonwoven, bioabsorbable web materials comprising a tri-block copolymer such as poly(glycolide-co-trimethylene carbonate) tri-block copolymer (PGA:TMC) are also useful (as described in U.S. Pat. No. 7,659,219; Biran et al.). Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL®. Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful substrates are polystyrenes, poly(methyl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics.

Subsequent coating that may be applied to the surface also include, but are not limited to, fluorinated polymers such as fluoropolymers, e.g expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like, as well as combinations thereof. and combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof may be useful.

This aspect of the invention is illustrated in Example 8, wherein a stent, to which had been applied a coating of the invention (dopa-BBA priming layer) was subsequently coated with a fluoro-copolymer. The adhesion of the coated stent (primed according to the invention) was found to be far superior to that of a stent which was coated directly with the fluoropolymer, as described in Example 9.

FIG. 6 illustrates a variant of Embodiment 2, wherein a subsequent coating has complementary functionality (CZ) to the photosensitive or thermosensitive group of component B (Z). Upon activation of group Z, component B forms covalent bonds with component A to form cross-linkages within the bulk of the coating, and Z groups which are in proximity to the subsequent coating will form covalent bonds with the subsequent coating. It should be noted that the above also applies to Embodiments 1a and 1b. This variant of the coating of the invention is expected to be particularly durable because of the cross-linking within the coating and because of the covalent bonding to the subsequent coating. In some embodiments, component A is also capable of reacting with the subsequent coating.

Thus, in certain embodiments, a subsequent coating which is applied on the surface has complementary functionality to the photosensitive or thermosensitive groups, which results in the coating of the invention being covalently bonded to a coating which is subsequently applied to the surface.

Thus, in embodiments wherein the coating of the invention is covalently bonded to subsequent coating, the subsequent coating can be expected to have enhanced durability (when compared with the durability of the same coating which is applied directly to the surface). In certain embodiments, the uniformity of the subsequent coating may also be improved (when compared with the uniformity of the same coating which is applied directly to the surface).

In one embodiment, the subsequent coating comprises a therapeutic agent. Suitably, the therapeutic agent is selected from the group consisting of an anti-thrombogenic agent, a hemostatic agent, an anti-angiogenic agent, an angiogenic agents, an anti-microbial agent, an anti-proliferative agent, a proliferative agent and an anti-inflammatory agent, or a combination thereof.

Other Aspects of the Coating

In one embodiment, the mass ratio of component A:component B is between 100:1 and 1:100, such as 100:1 to 1:5, such as 10:1 to 1:5, such as 5:1 to 1:2, such as 1:1.

The above mentioned ratios refer to the mass ratio of components A and B present in the reaction mixture before component B covalently bonds to component A. The ratio of components A and B present in the resulting coating may reasonably be expected to be substantially similar to the mass ratio of the individual components in the mixture of components before the coating is formed.

The dry thickness of the coating on the substrate can be controlled by limiting the quantities of components A and B and/or by limiting the time for step (a). Suitably, the coating is at least 100 nm thick when dry, for example at least 50 m, 25 nm, 10 nm, 5 nm, 1 nm, 0.5 nm or 0.1 nm. In one embodiment, the coating is 0.1-80 nm thick, for example 0.1-50 nm or 0.5-25 nm.

It should be noted that all aspects of the invention as described above and herein refer equally to the surface of the invention and the method of the invention.

The coating of the invention is formed by contacting the surface with a solution comprising components A and B. Suitably, the reaction solvent is an aqueous-solvent mixture such as a water-alcohol mixture or a water-buffer solution. Suitable alcohols include, but are not limited to, methanol, ethanol, propanol and isopropanol. Other suitable solvents include DMSO, DMF, acetone, acetonitrile, dioxane, THF, and the like. Suitable buffers include, but are not limited to, tris buffer and Trizma base (tris buffer and HCl).

The surface to be coated is first contacted with a solution of components A and B for a given length of time before being removed, and suitably dried (step (a)). If component A is water soluble but component B is not (or visa versa), then components A and B are separately dissolved in water and organic solvent, respectively, before being combined to form an emulsion. The photosensitive or thermosensitive moieties of component B are then activated by any suitable means. Certain photosensitive moieties can be activated by exposure to UV light. When UV light is used to initiate photoactivation, any suitable UV source can be used, for example a Fusion UV-lamp or Oriel UV-lamp providing UV-A and/or UV-B and/or UV-C radiation, or a pulsed UV lamp source (Xenon, XC-500) with broad UVA and UVB emission. Thermosensitive moieties may be activated using heat provided by any suitable means such as an oven or a heating element or forced air convection. When component B comprises a photosensitive moiety, suitably step (b) proceeds at room temperature.

Step (a) of the method (polymerisation reaction) is suitably carried out at pH 7-10, for example pH 7.5-9, or pH 8.5. As discussed above, a buffer such as tris buffer may be added to the solution to maintain the solution or emulsion at a particular pH. Other possible buffers include MES, ACES, PIPES, MOPSO, Bis-Tris propane, BES, MOPS, TES and HEPES. The pH of the solution can alternatively be adjusted using any suitable acid or base, such as HCl or NaOH, respectively.

In step (a) the reaction mixture must be open to the air (or have a source of $O_2$), as component A will generally self-polymerise via an oxidation process. The present inventors have found that, unusually, when component B comprises a benzophenone moiety as photosensitive moiety, step (b) (activation and formation of covalent bonds with component A) will proceed in the presence of polymerized Component A. As the presence of dopamine and polydopamine usually scavenge free radicals, which can lead to insufficient crosslinking, this is particularly surprising. See Ju et al., Biomacromolecules, 2011, Vol. 12, pages 625-632 which teaches that dopamine and polydopamine are free radical scavengers.

The rate of formation of the coating of components A and B in step (a) may be increased by the addition of an oxidant to the solution. Suitable oxidants include but are not limited to oxygen gas, ammonium persulfate and sodium persulfate.

The time required to form a coating of components A and B in step (a) will vary depending on the specific reaction conditions used. The coating of step (a) is preferably formed within a time period that is feasible for efficient manufacture. For example, within 48 hours, 24 hours, 12 hours, 6 hours, 5 hours, 4 hours, 3 hours, 2 hours, 1 hour or 30 min. As a general principle, the longer the polymerisation time, the thicker the coating. The time required to activate the photosensitive or thermosensitive moieties of component B in order to form covalent bonds with component A (step (b) of the method) will also vary depending on the specific reaction conditions used, but the time required for step (b) will usually be shorter than the time required for step (a). For example, when component B comprises photosensitive moieties which are activated by UV light, the coated surface of step (a) only requires UV irradiation for around 6 minutes.

Further Aspects of the Method of the Invention

The speed of the self-polymerisation reaction in step (a) of the methods of the invention may be increased by the addition of an oxidant such as a stream of $O_2$, ammonium persulfate or ammonium persulfate.

Prior to coating, the surface of the substrate can be cleaned or pretreated in order to improve adhesion of the coating (be that the coating of the invention or a coating comprising CZ groups). Prior cleaning or pretreatment of the surface may also improve the uniformity of the coating.

Suitable cleaning agents or pre-treatment agents include solvents as ethanol or isopropanol (IPA), solutions with high pH such as solutions comprising a mixture of an alcohol and an aqueous solution of a hydroxide compound (e.g. sodium hydroxide), sodium hydroxide solution per se, solutions containing tetramethyl ammonium hydroxide (TMAH), basic Piranha (ammonia and hydrogen peroxide), acidic Piranha (a mixture of sulfuric acid and hydrogen peroxide), and other oxidizing agents including sulfuric acid and potassium permanganate or different types of peroxysulfuric acid or peroxydisulfuric acid solutions (also as ammonium, sodium, and potassium salts e.g. ammonium persulfate), or combinations thereof.

Properties of the Coating

Coatings according to the invention, in at least some embodiments, are expected to have one or more advantages of:
- having high durability
- having good coating uniformity;
- being stable to oxidation degradation, erosion and depolymerisation
- being stable to sterilisation;
- wide applicability, as the coating is surface independent.

DEFINITIONS AND ABBREVIATIONS

'$C_1$-$C_8$ alkyl' is defined as a straight or branched aliphatic carbon chain containing 1-8 carbon atoms, for example methyl, ethyl, n-propyl, isopropyl, n-butyl, isobutyl, t-butyl, pentyl, isopentyl, hexyl, heptyl and octyl and the corresponding alkylene radicals such as methylene, ethylene, etc.

'$C_2$-$C_8$ alkenyl' is defined as a straight or branched aliphatic carbon chain containing 2-8 carbon atoms and at least one carbon-carbon double bond. Examples include, but are not limited to, vinyl, acrylate, acrylamide, methacrylate, methacrylamide, and the like.

'$C_2$-$C_8$ alkynyl' is defined as a straight or branched aliphatic carbon chain containing 2-8 carbon atoms and at least one carbon-carbon triple bond.

ABBPMA 3-amido(4-benzoylbenzoyl)propyl methacrylamide
AIBN 2,2'-azobis(2-methylpropionitrile)
BP benzophenone
BBA-Cl 4-benzoylbenzyol chloride
dopa-BBA dopamine benzoyl benzamide
DMSO dimethyl sulfoxide
d.i. deionised
GPC gas phase chromatography
hr hour
IPA isopropanol
min minute
MES 2-(N-morpholino)ethanesulfonic acid
ePTFE expanded polytetrafluoroethylene
PEG polyethylene glycol
TFE-co-VAc copolymer comprising tetrafluoroethylene-co-vinyl acetate
tris tris(hydroxymethyl)aminomethane
tris-BBA tris-[amino(ethylbenzoylbenzamide)]
QCM quartz crystal microbalance
VP-co-BBA poly(vinylpyrrolidone-co-amido(4-benzoylbenzoyl)propyl methacrylamide

EXAMPLES

General Procedures

Chemicals

Dopamine HCl, 4-benzoylbenzoic acid, thionyl chloride, N-vinyl pyrrolidone and AIBN were purchased from Sigma. Tris(2-aminoethyl)amine, 4-aminobenzophenone, 4,4'-diaminobenzophenone, 4,4'-dihydroxybenzophenone, 3,4-diaminobenzophenone and eugenol were purchased from Aldrich. 3-Aminopropylmethacrylamide was purchased from Polysciences.

Materials

Single wire nitinol stents interconnected by an ePTFE structure were obtained from W.L. Gore & Associates, Inc., Flagstaff, Ariz. under the trade name GORE® TIGRIS Vascular Stent. Quartz glass slides (72250-03) were purchased from Electron Microscopy Sciences, Hatfield, Pa. ePTFE membrane (GMM-406, GORE® Microfiltration Media) was supplied by W.L. Gore & Associates, Inc., Flagstaff, Ariz. Pebax tubing (72D) was purchased from Arkema, King of Prussia, Pa.). FEP tubing (600036-05) was purchased from Zeus, Orangeburg, S.C.

Evaluation Methods

The parameter being evaluated by each method is given in parentheses.

Time-Of-Flight Secondary Ion Mass Spectrometry (TOF-SIMS; Coating Composition)

TOF-SIMS uses a pulsed primary ion beam to desorb and ionize species from a sample surface. The resulting secondary ions are accelerated into a mass spectrometer, wherein they are mass analyzed by measuring their time-of-flight from the sample surface to the detector. For coatings of the present invention, one would expect to detect fragments of component B, especially tertiary hydroxyl groups (a reaction product in embodiments where component B abstracts hydrogen via activation of a ketone group, Scheme 1, supra).

Nanomechanical Testing (Coating Coverage and Adhesion)

This testing involved nanoscratch testing, imaging of the scratch region, and nanoindent testing, to record quasi-static reduced modulus values, which were then converted into adhesive critical failure load values (a routine test procedure which is well known to the skilled person). Testing was carried out using a Hysitron 950 Triboindenter (Hysitron Inc., Eden Prairie, Minn.). 5 stents of each coating formulation were tested at random locations. This technique can be used to investigate the extent of cross linking (formed by component B forming covalent bonds with component A) throughout the thickness of the coating. If only the outermost (or innermost) sections of the coating are cross-linked, then these sections will have a different modulus and/or adhesion strength, while a coating which is cross-linked throughout its full thickness will have a uniform modulus and/or adhesion strength.

X-Ray Photoelectron Spectroscopy with Depth Profiling (XPS) (Coating Composition)

Samples were irradiated with mono-energetic X-rays causing photoelectrons to be emitted from the top 1-10 nm of the sample surface. An electron energy analyzer determined the binding energy of the photoelectrons. Qualitative and quantitative analysis of all elements except hydrogen and helium was possible, at detection limits of ~0.1-0.2 atomic percent. Analysis spot sizes ranged from 10 µm to 1.5 mm. It is also possible to generate surface images of features using elemental and chemical state mapping. Depth profiling was possible using angle-dependent measurements to obtain non-destructive analyses within the top 10 nm of a surface, or throughout the coating depth using destructive analysis such as ion etching or C60 sputtering. Carbon, oxygen, and nitrogen X-ray spectra were normalized to the carbon 285 eV peak. For coatings of the present invention comprising aryl ketone moieties, in particular benzophenone, the aromatic groups were detectable on the carbon spectrum at 290-293 eV.

Visual Inspection (Coating Coverage and Adhesion)

Coatings of the invention, at least in some embodiments were coloured. Coatings wherein component A was dopamine may vary in colours from dark grey through to yellow. The coating colouring was used to assess the durability of the coating, as if the coating was degraded, eroded or depolymerized then the colour changed. Degradation, erosion and depolymerisation was indicated by a lighter coloured coating, a less intense colour or the absence of the original colour.

Scanning Electron Microscopy (SEM) (Coating Coverage and Adhesion)

SEM images of coated samples were captured using a Zeiss Supra 35 VP SEM. SEM imaging and EDS (energy dispersive X-ray spectroscopy) were used to provide information on the extent, distribution, and uniformity of the coating.

Quartz Crystal Microbalance (QCM) (Coating Coverage, Thickness and Adhesion)

Quartz Crystal Microbalance techniques (QCM) may be used to evaluate the thickness of coating layer. Comparing the thickness before and after subjecting the surface to oxidation conditions provides an indication of the coating adhesion.

Particulation (Coating Adhesion)

Particulation on the surface of the coating may be indicative of erosion or degradation of the coating, and may be observed after purposeful abrasion of the coated surface in a test protocol, intended to mimic in-service use. Particles in the collection media can be analyzed by an Accusizer Particle Sizer (780/SIS PSS NICOMP, Santa Barbara, Calif. USA) according to test method described by United States Pharmacopeia (USP) monograph 788 for small volume injectables. More durable coatings will have less particulation after abrasion.

Example 1a

Evaluation of Dopamine Polymerization in Water Buffer Compared to Water/Alcohol Emulsion The ability of dopamine to coat a substrate was examined using systems involving aqueous buffer or water/alcohol emulsion. The substrate comprised tubing of Pebax72D loaded with 20% w/w $BaSO_4$ powder, that had been cleaned by sonication in isopropanol for 10 min and air dried.

An aqueous tris buffer was formed by dissolving tris at 10 mM in deionized water and adjusting the pH to 8.5 with HCl. A water/alcohol emulsion was formed by mixing 1 part aqueous tris buffer (50 mM) to 4 parts methanol, to give a final concentration of 10 mM Trizma, and adjusting the pH to 8.5 with HCl. Dopamine-HCl was dissolved at 2 mg per 5 ml in the aqueous buffer and in the water/alcohol emulsion. A 4 cm sample of the Pebax/$BaSO_4$ tubing was immersed into 5 ml of each dopamine solution to completely wet the sample. Air was bubbled through each solution for 20 seconds. The solutions were left undisturbed for 72 hr.

Sample substrates were vigorously rinsed in deionized water and dried in an oven at 50° C. The normally bright white Pebax/$BaSO_4$ tubing was a light-to-dark grey colour for both solutions, indicating deposition of a polydopamine coating stable to water rinsing.

Example 1b

XPS Analysis of Coatings Comprising Dopamine Polymerized in Water Compared to Water/Alcohol Emulsion The coated samples of Example 1a were examined with X-ray photoelectron spectroscopy. Carbon, oxygen, and nitrogen x-ray spectra were normalized to the carbon 285 eV peak. In the regions of 280-298 eV (carbon), 524-540 eV (oxygen), and 392-410 eV (nitrogen), the dopamine/buffer spectrum overlapped the dopamine/emulsion spectrum, indicating that the polydopamine coating is unaltered by the use of aqueous buffer or water-alcohol emulsion.

Example 2a

Synthesis of Dopamine Benzoyl Benzamide ("Dopa-BBA")

4-Benzoylbenzyol chloride was first prepared by the reaction of 4-benzoylbenzoic acid with excess thionyl chloride in refluxing anhydrous dimethylformamide (note: all reactions involving photosensitive reagents were performed in a UV/blue light-shielded fume hood). The 4-benzoylbenzoyl chloride product ("BBA-Cl") was recovered by rotary evaporation and recrystallization from hexane/toluene (4:1).

The BBA-Cl product was dissolved in pyridine:chloroform (1:4). Dopamine HCl was dissolved in chloroform. The two solutions were reacted (BBA-Cl in excess) under argon for about 24 hours with stirring. The resulting suspension was washed with aqueous acid and with water, dried over sodium sulfate, and the organic solvent removed under rotary evaporation. The dopamine benzoyl benzamide ("dopa-BBA") product was recrystallized from toluene:chloroform (4:1). Proton-NMR characterization demonstrated 85% purity, with the remainder comprising 4-benzoylbenzoic acid and dopamine Example 2b Synthesis of tris-[amino(ethylbenzoylbenzamide)] ("tris-BBA")

The BBA-Cl of Example 2a was dissolved in chloroform. Tris(2-aminoethyl)amine was dissolved in aqueous base. The BBA-Cl solution was added (in excess) to the tris(2-aminoethyl)amine solution, dropwise with vortexing, and reacted an additional 30 min with vortexing. The emulsion was allowed to separate, the organic layer washed with aqueous base, dried over sodium sulfate, and the organic solvent removed under rotary evaporation. The final product, tris(benzoylbenzamide ethyl)amine ("tris-BBA"), was characterized by proton NMR.

Example 2c

Synthesis of 3-amido(4-benzoylbenzoyl)propyl methacrylamide "ABBPMA"

A monomer comprising a benzophenone moiety and a methacrylamide moiety was prepared.

The BBA-Cl of Example 2a was reacted with 3-aminopropylmethacrylamide in chloroform/triethylamine (5:1) for 4.5 hrs. The solution was washed with dilute aqueous HCl and then water, and the organic fraction dried over sodium sulfate. The product, 3-amido(4-benzoylbenzoyl)propyl methacrylamide ("ABBPMA"), was recovered by rotary evaporation and recrystallization from toluene/chloroform (4:1).

Example 2d

Synthesis of poly(vinylpyrrolidone-co-amido(4-benzoylbenzoyl)propyl methacrylamide ("VP-co-BBA")

The title polybenzophenone copolymer VP-co-BBA was prepared by free radical polymerization of the ABBPMA form Example 2c with N-vinyl pyrrolidone (freshly vacuum distilled), using AIBN initiator, at a mass ratio of 92.3:7.5:0.2 respectively, in dimethylsulfoxide, under argon, 65° C., 3 days. The copolymer product was recovered via sequential dialysis (MWCO 10 KDa) against toluene, ethanol, then water, and lyophilized. The copolymer product was characterized by proton NMR and GPC. The final product, poly(vinylpyrrolidone-co-amido(4-benzoylbenzoyl)propyl methacrylate) ("VP-co-BBA"), contained 2.7% mole fraction benzophenone-bearing groups, and a number average molecular weight of 284 KDa.

Example 3

Coating of Dopamine with Functionalized UV Compounds onto Various Substrates

The following functionalized UV compounds were examined for their ability to engraft and UV crosslink into a polydopamine coating:
dopa-BBA (Example 2a)
tris-BBA (Example 2b)
ABBPMA monomer (Example 2c)
VP-co-BBA (Example 2d)
4-aminobenzophenone ("4NH$_2$")
Eugenol
4,4'-diaminobenzophenone ("44'NH$_2$")
4,4'-dihydroxybenzophenone ("44'OH")
3,4-diaminobenzophenone ("34NH$_2$").

Briefly, the functionalized UV compound was dissolved in methanol, dopamine-HCl was dissolved in Trizma buffer, and the two combined with vortexing. Final concentrations were 10 mM Trizma, 2 mg dopamine, and 10 mg functionalized UV compound per 5 ml solution. A 4 cm sample of sonicated and dried Pebax/BaSO$_4$ tubing was immersed into 5 ml of each solution to completely wet the sample. Air was bubbled through each solution for 20 sec. The solutions were left undisturbed for 48 hr. Sample substrates were vigorously rinsed in deionized water, methanol, water:methanol, and finally water and were then dried in an oven at 50° C.

Example 4

UV Curing of Example 1a and 3

The coated tubing samples of Example 3 were exposed to UV light to effect covalent crosslinking of the polydopamine coating. The coated tubing samples of Example 1a were also exposed to UV light as a comparison.

The coated tubing samples of Example 1a and 3 were exposed to a pulsed UV lamp source (Xenon, XC-500) with broad UVA and UVB emission. They were exposed to 15 mW/cm$^2$ intensity light (at 254 nm) for 6 minutes with 60 rpm axial rotation to ensure even exposure along the outer circumference of the coated tubing sample, for a total dose of 2.7 J/cm$^2$.

Example 5

Oxidation Stability of Examples 1a, 3 and 4

It is known that oxidation, such as immersion into hypochlorite, can degrade polydopamine coatings (Del Frari, Polym Degrad Stab, 97, 1844, 2012; B P Lee, Ann Rev Mater Res, 41, 99, 2011). To evaluate stability against oxidation as a dependence upon incorporation of the functionalized UV compound, the non-UV-cured tubing samples of Examples 1a and 3 and the UV-cured tubing samples of Example 4 were immersed in NaClO (Clorox) dissolved in water (6% w/v), for 15 sec, rinsed vigorously in deionized water, then air dried in an oven at 50° C. The colour of the coating against the white background of the tubing was noted.

TABLE 1

| no UV curing | | |
|---|---|---|
| Coating composition | Colour before oxidation | Colour after oxidation |
| dopa/buffer | brown-grey | None |
| dopa/alcohol | dark gray | None |
| tris-BBA | brown-gray | None |
| VP-co-BBA | brown-gray | None |
| ABPMA | yellow-brown | faint brown |

The results of Table 1 demonstrate that the dopamine coatings, and the dopamine coatings comprising a functionalized UV compound that were not irradiated with UV to induce covalent crosslinking of the coating, were not resistant to oxidation by hypochlorite.

TABLE 2

| UV curing | | |
|---|---|---|
| Coating composition | Colour before oxidation | Colour after oxidation |
| dopa/buffer | brown-grey | None |
| dopa/alcohol | dark grey | None |
| dopa-BBA | brown-yellow | brown-yellow |
| Eugenol | dark brown | dark brown |
| 44'NH$_2$ | yellow | yellow |
| 44'OH | yellow-orange | yellow-orange |
| 34NH$_2$ | yellow | yellow |
| 4NH$_2$ | yellow-brown | yellow-brown |
| tris-BBA | brown-grey | brown-grey |
| VP-co-BBA | brown-grey | brown-grey |
| ABPMA | yellow-brown | yellow-brown |

The results of Table 2 demonstrate that dopamine coatings which were irradiated with UV were not resistant to oxidation by hypochlorite. The results further demonstrate that the dopamine coatings comprising a functionalized UV compound that were irradiated with UV to induce covalent crosslinking of the coating, were resistant to oxidation by hypochlorite, as indicated by no change in their coloration.

It was observed that coatings retained their original colour over time periods at least as long as 8 months, even after exposure to bleach. As discussed in the detailed description, to the best of the inventors' knowledge this Example is the first demonstration of polydopamine coatings with stable colours other than grey or black.

Example 6

Coating of Other Substrates

Other substrates were coated with dopamine from emulsion, and with dopamine comprising UV functionalized compounds. These coated substrates were coated as per Examples 1a and 3, and UV cured as per Example 4.

A variety of substrates were coated, including quartz glass slides, ePTFE membrane, Pebax tubing (72D), FEP tubing (600036-05, Zeus, Orangeburg, S.C.), and low density polyethylene (LDPE) tubing.

After coating and UV curing, the substrates had different colours, indicating the deposition of the dopamine or the dopamine comprising UV functionalized compounds. The samples were exposed to hypochlorite as per Example 5. The coated samples comprising dopamine prepared as per Example 1a were unstable to oxidation as indicated by a loss of colour. The coated samples comprising dopamine comprising UV functionalized compounds, and exposed to UV, were stable to oxidation, as indicated by a stable colour.

Example 7

Priming of a Stent with a Dopa-BBA Primer Layer

The dopa-BBA of Example 2a was primed onto a single wire nitinol stent interconnected by an ePTFE structure. The dopa-BBA was dissolved (3.5 mg per 5 ml) in an aqueous buffer as per Example 2a. The stent was then immersed into the dopa-BBA solution, with gentle shaking, for about 24 hr. The stent was rinsed multiple times with deionized water, and dried at 60° C. for about 1 hr. The coated stent was exposed to UV as per Example 4.

Example 8

Coating of a Stent Comprising a Dopa-BBA Primer Layer with a Topcoat Comprising a Fluoro-Copolymer The dopa-BBA primed stent of Example 7 was coated with a fluoro-copolymer comprising tetrafluoroethylene-co-vinyl acetate. As such, a copolymer comprising tetrafluoroethylene-co-vinyl acetate ("TFE-co-VAc"), at a mole ratio of 20:80, was first prepared. To a nitrogen purged 1 L pressure reactor under vacuum were added d.i. water (500 g), 20% aqueous ammonium perfluorooctanoate (2 g), distilled vinyl acetate (30 ml), n-butanol (10 g), and ammonium persulfate (0.2 g). Tetrafluoroethylene monomer was fed into the reactor until the reactor pressure reached 1500 KPa. The mixture was stirred and heated to 50° C. When a pressure drop was observed, vinyl acetate (25 ml) was slowly fed into the reactor. The reaction was stopped when the pressure dropped another 150 KPa after vinyl acetate addition. The copolymer was obtained from freeze-thaw coagulation of the latex emulsion, cleaned with methanol/water extraction, and dried under vacuum. The TFE-co-VAc copolymer was dissolved at 1.5 mg/ml in a solution of methylpentanone/cyclohexanone/acetone (1:1.5:7.5).

The primed stent of Example 7 was coated with the TFE-co-VAc solution, by evenly spraying a fine mist of the TFE-co-VAc solution onto the primed stent with rotation. The solvent was removed by heating at 120° C. for 10 min. An average of 1.5 mg of copolymer was coated onto the stents at an average thickness of 0.7 um For comparison, an unprimed stent not comprising the dopa-BBA primer was coated with the TFE-co-VAc solution. The fine mist was observed largely not to adhere to the stent surface, and produced a highly discontinuous coating that readily flaked off the stent surface.

Example 9

Adhesion of a Stent Primed with Dopa-BBA and Coated with TFE-co-VAc

Adhesion testing of the primed and unprimed stents and coated with TFE-co-VAc was performed by nanomechanical testing (Hysitron, Eden Prairie, Minn.).

For those stents primed with dopa-BBA, exposed to UV radiation, and coated with TFE-co-VAc, the average critical load failure was 26.1 mN with a standard deviation of about 10% among the tested locations. For those stents not primed with dopa-BBA, and coated with TFE-co-VAc, nanomechanical testing was not possible due to the poor quality of the coating.

These results demonstrate the H-abstraction capability of the dopa-BBA primer layer improved the coating consistency of the sprayed topcoat solution, improved the adhesive strength of the topcoat layer, and generated a homogeneous coating with little deviation in adhesive strength across the stent surface area.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A surface having a coating comprising a cross-linked copolymer of components A and B, wherein component A is a molecule capable of self polymerisation comprising catechol functionality and amine and/or amide and/or hydroxyl functionality; and component B is a molecule comprising one or more groups capable of participating in the polymerisation of component A, wherein said molecule comprises one or more photosensitive or thermosensitive moieties capable of forming covalent bonds with component A, at least some of which moieties form covalent bonds with component A in the copolymer; and wherein component B is dopamine benzoyl benzamide.

2. A surface having a coating according to claim 1, wherein the surface is the surface of a substrate comprising a medical device.

3. A surface having a coating according to claim 2, wherein the medical device is selected from the group consisting of stents including bifurcated stents, balloon expandable stents and self-expanding stents, stent-grafts including bifurcated stent-grafts, grafts including vascular grafts and bifurcated grafts, dialators, vascular occluders, embolic filters, embolectomy devices, catheters including microcatheters, central venous catheters, peripheral intravenous catheters and hemodialysis catheters, artificial blood vessels, sheaths including retractable sheaths, blood indwelling monitoring devices, artificial heart valves, pacemaker electrodes, guidewires, cardiac leads, cardiopulmonary bypass circuits, cannulae, plugs, drug delivery devices, balloons, tissue patch devices and blood pumps.

* * * * *